US011253146B2

(12) United States Patent
Muyo et al.

(10) Patent No.: US 11,253,146 B2
(45) Date of Patent: Feb. 22, 2022

(54) OPHTHALMIC DEVICE

(71) Applicants: OPTOS PLC, Dunfermline (GB);
NIKON CORPORATION, Tokyo (JP)

(72) Inventors: Gonzalo Muyo, Scotland (GB);
Alistair Gorman, Scotland (GB);
Makoto Ishida, Tokyo (JP)

(73) Assignee: OPTOS PLC, Dunfermline (GB)

( * ) Notice: Subject to any disclaimer, the term of this patent is extended or adjusted under 35 U.S.C. 154(b) by 397 days.

(21) Appl. No.: 16/335,174

(22) PCT Filed: Oct. 10, 2017

(86) PCT No.: PCT/EP2017/075852
§ 371 (c)(1),
(2) Date: Mar. 20, 2019

(87) PCT Pub. No.: WO2018/069346
PCT Pub. Date: Apr. 19, 2018

(65) Prior Publication Data
US 2021/0275010 A1  Sep. 9, 2021

(30) Foreign Application Priority Data
Oct. 11, 2016  (JP) .............................. JP2016-200482

(51) Int. Cl.
*A61B 3/00* (2006.01)
*A61B 3/10* (2006.01)
*A61B 3/12* (2006.01)

(52) U.S. Cl.
CPC .......... *A61B 3/0091* (2013.01); *A61B 3/0008* (2013.01); *A61B 3/102* (2013.01); *A61B 3/1025* (2013.01); *A61B 3/12* (2013.01)

(58) Field of Classification Search
CPC ....... A61B 3/0091; A61B 3/0008; A61B 3/12; A61B 3/1025; A61B 3/102; G06K 9/0061; G06T 7/0012
(Continued)

(56) References Cited

U.S. PATENT DOCUMENTS 5,815,242 A    9/1998  Anderson et al.
6,257,722 B1 *  7/2001  Toh .......................... A61B 3/152
                                                                    351/208
(Continued)

FOREIGN PATENT DOCUMENTS

JP    3490088 B2     1/2004
JP    2007-089916 A  4/2007
(Continued)

OTHER PUBLICATIONS

Int'l Search Report and Written Opinion from Int'l Appl'n No. PCT/EP2017/075852, dated Dec. 11, 2017.
(Continued)

*Primary Examiner* — Mohammed A Hasan
(74) *Attorney, Agent, or Firm* — DeLucia Mlynar & Associates LLP

(57) ABSTRACT

An ophthalmic device comprising a light source to emit fixation target light, and a reflecting face to reflect scanning light emitted by an emission section and scan the scanning light in a specific direction by changing orientation, the emission section being a scanning light source different to the light source. A concave mirror face is disposed so scanning light reflected by the reflecting face is incident on a subject's eye ocular fundus when the eye is at the concave mirror's focal point, and is arranged such that, when the eye is at the concave mirror's focal point, and when the light source emits fixation target light, that light and scanning light are simultaneously incident on the ocular fundus via (Continued)

different optical paths propagating via the concave mirror face and focal point, the target fixation light following a predetermined optical path for fixing the subject's eye gaze.

13 Claims, 27 Drawing Sheets

(58) Field of Classification Search
USPC .......................................................... 351/206
See application file for complete search history.

(56) References Cited

U.S. PATENT DOCUMENTS

| | | |
|---|---|---|
| 7,959,290 B2 | 6/2011 | Cairns et al. |
| 9,454,817 B2 | 9/2016 | Clifton et al. |
| 2007/0030449 A1 | 2/2007 | Liang |
| 2010/0149489 A1 | 6/2010 | Kikawa et al. |
| 2012/0092616 A1 | 4/2012 | Peyman |
| 2012/0257166 A1 | 10/2012 | Francis et al. |
| 2013/0135583 A1 | 5/2013 | Gray et al. |
| 2013/0335703 A1 | 12/2013 | Creasey et al. |
| 2014/0293227 A1 | 10/2014 | Yoshida |
| 2014/0327882 A1 | 11/2014 | Muyo et al. |
| 2015/0028707 A1 | 1/2015 | Kim et al. |
| 2015/0042950 A1 | 2/2015 | Yamazaki |
| 2015/0216408 A1 | 8/2015 | Brown et al. |
| 2015/0282707 A1* | 10/2015 | Tanabe ................. A61B 3/14 351/206 |
| 2016/0089024 A1 | 3/2016 | Katashiba |
| 2016/0270656 A1* | 9/2016 | Samec ................. A61B 3/024 |
| 2020/0237417 A1* | 7/2020 | Blacklidge .......... A61B 17/8085 |

FOREIGN PATENT DOCUMENTS

| | | |
|---|---|---|
| JP | 2008-289579 A | 12/2008 |
| JP | 5330236 B2 | 10/2013 |
| JP | 2015-205176 A | 11/2015 |
| JP | 2016-067551 A | 5/2016 |
| WO | 95/13012 A2 | 5/1995 |
| WO | 2008/009877 A1 | 1/2008 |

OTHER PUBLICATIONS

Japanese Office Action Issued in Japanese Application No. 2019-515968, dated Jun. 16, 2020 . [English Translation of Japanese Office Action Attached].

* cited by examiner

OPHTHALMIC DEVICE

This application is a National Stage Application of International Application No. PCT/EP2017/075852, filed 10 Oct. 2017, which claims benefit of Serial No. 2016-200482, filed 11 Oct. 2016 in Japan and which applications are incorporated herein by reference. To the extent appropriate, a claim of priority is made to each of the above disclosed applications.

TECHNICAL FIELD

The technology of the present disclosure relates to an ophthalmic device.

BACKGROUND

For convenience of explanation, optical coherence tomography is referred to as "OCT", and scanning laser ophthalmoscopy is referred to as "SLO" below.

Patent Document 1 describes an ocular fundus examination device provided with an OCT unit that generates an image using OCT. In the OCT unit described by Patent Document 1, a tomographic image that is an image taken in the thickness direction of the membrane of the ocular fundus of a subject's eye is generated based on an image signal detected by charge coupled devices (CCDs).

A liquid crystal display (LCD) is housed in the ocular fundus examination device of Patent Document 1, and the LCD displays a fixation target to cause the gaze of the subject's eye to be fixed in a specific orientation in a case in which the ocular fundus is imaged by the OCT unit. Light from the LCD is incident to the subject's eye via an optical system that includes lenses and mirrors, such that the fixation target is projected onto the ocular fundus of the subject's eye.

RELATED DOCUMENTS

Related Patent Documents

Patent Document 1: Japanese Patent Application Laid-Open No. 2008-289579

SUMMARY OF INVENTION

The present invention provides an ophthalmic device comprising a light source arranged to emit a fixation target light, and a reflecting face arranged to reflect scanning light emitted by an emission section and to scan the scanning light in a specific direction by changing orientation, the emission section being a source of the scanning light that is different to the light source. The ophthalmic device further comprises a concave mirror face disposed such that the scanning light reflected by the reflecting face is incident on the ocular fundus of a subject's eye when the subject's eye is placed at a focal point of the concave mirror during use of the ophthalmic device, and is arranged such that, when the subject's eye is placed at the focal point of the concave mirror during use of the ophthalmic device and when the light source emits the fixation target light, the fixation target light and the scanning light are simultaneously incident on the ocular fundus via different optical paths both propagating via the concave mirror face and the focal point, the target fixation light following a predetermined optical path for fixing the gaze of the subject's eye.

The ophthalmic device according to an embodiment may be arranged such that, when the subject's eye is placed at a focal point of the concave mirror during use of the ophthalmic device and when the light source emits the fixation target light, the fixation target light and the scanning light are simultaneously incident on the ocular fundus via different optical paths both passing via the reflecting face, the concave mirror face and the focal point, the ophthalmic device further comprising a controller arranged to control emission of the target fixation light by the light source such that the fixation target light follows the predetermined optical path for fixing the gaze of the subject's eye.

The ophthalmic device according to the above embodiment may further comprise at least one further light source arranged such that, when the subject's eye is placed at the focal point of the concave mirror during use of the ophthalmic device and when each of the at least one further light source emits the fixation target light, the respective fixation target light and the scanning light are simultaneously incident on the ocular fundus via different optical paths both going via the concave mirror face and the focal point, the optical path of the respective fixation target light not passing via the reflecting face. The controller may be arranged to select a light source from the light sources and control emission of the fixation target light by the selected light source, based on information indicative of at least one of the orientation of the reflecting face, a range of orientation of the reflecting face, and a speed at which the orientation of the reflecting face changes, such that the fixation target light emitted by the selected light source follows a predetermined optical path for fixing the gaze of the subject's eye.

The ophthalmic device according to the above embodiment may alternatively further comprise at least one further light source arranged such that, when the subject's eye is placed at the focal point of the concave mirror during use of the ophthalmic device and when each of the at least one further light source emits the fixation target light, the respective fixation target light and the scanning light are simultaneously incident on the ocular fundus via different optical paths both going via the reflecting face, the concave mirror face and the focal point. The controller may be arranged to select a light source from the light sources and control emission of the fixation target light by the selected light source, based on information indicative of one of the orientation of the reflecting face, a range of orientation of the reflecting face, and a speed at which the orientation of the reflecting face changes, such that the fixation target light emitted by the selected light source follows a predetermined optical path for fixing the gaze of the subject's eye.

Any of the ophthalmic devices set out above may be arranged such that, when the subject's eye is placed at the focal point of the concave mirror during use of the ophthalmic device and when each light source emits fixation target light, the respective fixation target light and the scanning light are simultaneously incident on different locations on the ocular fundus via different optical paths both going via the concave mirror face and the focal point.

In the ophthalmic device according to the embodiment, or in any of the variants thereof set out above, the controller may be arranged to control emission of the target fixation light by each light source such that the light source emits the fixation target light only when the reflecting face is orientated in a predetermined orientation, said predetermined orientation being adjustable so as to vary a location on the ocular fundus onto which the fixation target light is emitted.

Any of the ophthalmic devices set out above may further comprise a second reflecting face that is disposed at a first position separated from an optical pathway of the scanning light in a case in which the scanning light is emitted onto a peripheral region of the ocular fundus, and may be arranged to reflect fixation target light onto the ocular fundus along the predetermined optical path via the concave mirror face when the subject's eye is placed at the focal point of the concave mirror during use of the ophthalmic device. In this case, the second reflecting face may be movable between the first position and a second position, the second position being separated from an optical pathway of the scanning light in a case in which the scanning light is emitted onto a central region of the ocular fundus, and the ophthalmic device may further comprise a moving mechanism arranged to move the second reflecting face between the first position and the second position, and a controller arranged to control the moving mechanism, and to control the light source that is arranged to emit the fixation target light which is reflected from the second reflecting face, such that the second reflecting face is disposed at the first position and said light source is lit up in a case in which the orientation of the first reflecting face is an orientation causing the scanning light to be emitted onto the peripheral region, and such that the second reflecting face is disposed at the second position in a case in which the orientation of the first reflecting face is an orientation causing the scanning light to be emitted onto the central region. Where the above-described embodiment comprises these further features, the controller may be arranged to select a light source of the light sources, control emission of the fixation target light by the selected light source, and control the positioning of the second reflecting surface by the moving mechanism, based on information indicative of at least one of the orientation, a range of orientation of the reflecting face, and a speed at which the orientation of the reflecting face changes, such that the fixation target light emitted by the selected light source follows a predetermined optical path for fixing the gaze of the subject's eye.

Alternatively, any of the ophthalmic devices set out above may further comprise a second light source that is disposed at a first position separated from an optical pathway of the scanning light in a case in which the scanning light is emitted onto a peripheral region of the ocular fundus, and be arranged to emit fixation target light onto the ocular fundus along a predetermined optical path via the concave mirror face when the subject's eye is placed at the focal point of the concave mirror during use of the ophthalmic device. In a modification, the second light source may be movable between the first position and a second position, the second position being separated from an optical pathway of the scanning light in a case in which the scanning light is emitted onto a central region of the ocular fundus, and the ophthalmic device may further comprise a moving mechanism arranged to move the second light source between the first position and the second position, and a controller arranged to control the moving mechanism and the emission of target fixation light by the second light source such that the second light source is disposed at the first position and lit up in a case in which the orientation of the first reflecting face is an orientation causing the scanning light to be emitted onto the peripheral region, and such that the second light source is disposed at the second position in a case in which the orientation of the first reflecting face is an orientation causing the scanning light to be emitted onto the central region. Where the aforementioned modification is applied to the above-described embodiment, the controller may be arranged to select a light source of the light sources, control emission of the fixation target light by the selected light source, and control the positioning of the second light source by the moving mechanism, based on information indicative of at least one of the orientation, a range of orientation of the reflecting face, and a speed at which the orientation of the reflecting face changes, such that the fixation target light emitted by the selected light source follows a predetermined optical path for fixing the gaze of the subject's eye.

Any of the ophthalmic devices set out above may be arranged such that, when the subject's eye is placed at the focal point of the concave mirror during use of the ophthalmic device, the light source is arranged to emit the fixation target light such that the fixation target light incident on the ocular fundus is perceived by the subject as a continuous lighting-up in one position due to an after-image effect.

DESCRIPTION OF EMBODIMENTS

Figure 1:
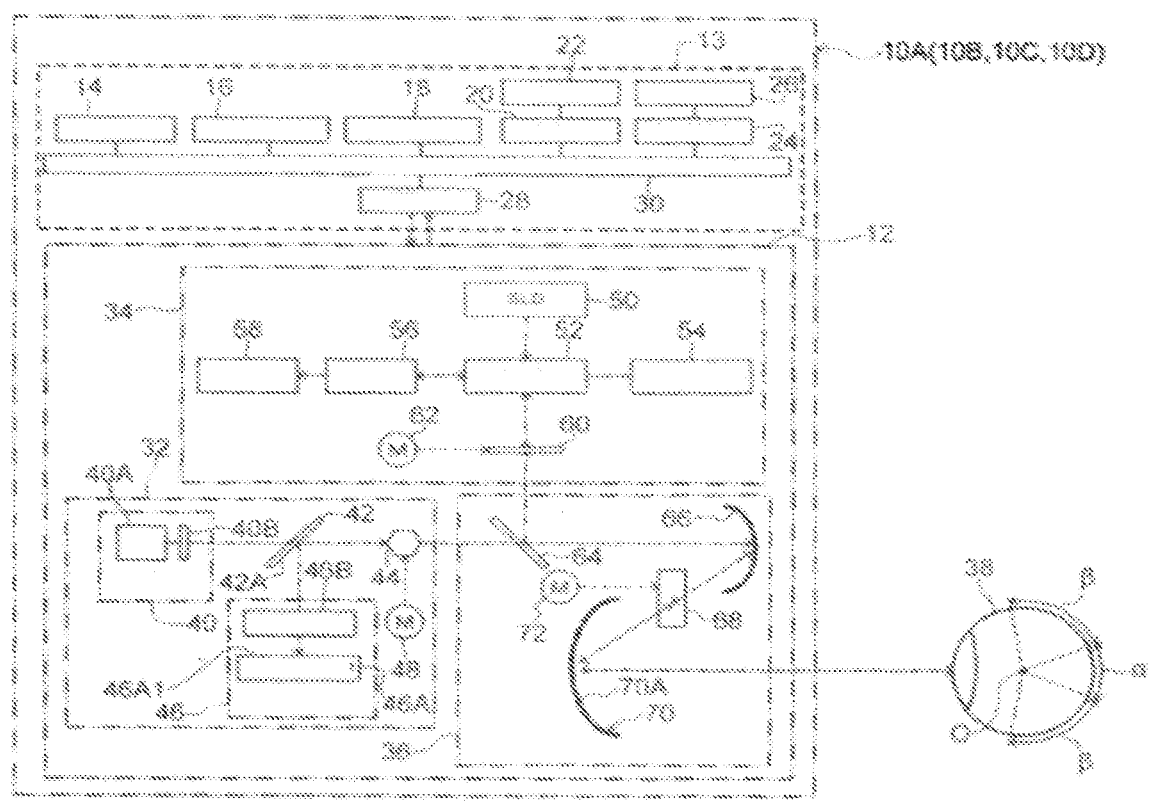
FIG. 1 is a block diagram illustrating an example of an overall configuration of an ocular fundus examination device according to a first to a fourth exemplary embodiment.

Explanation follows regarding an example of an exemplary embodiment according to the present invention with reference to the attached drawings.

An embodiment of the present invention provides an ocular fundus examination device, as an example of an ophthalmic device, which is capable of implementing presentation of a fixation target corresponding to a widened angle of a region of ocular fundus onto which light is emitted from the light source for imaging the ocular fundus.

An ocular fundus examination device of a first embodiment of the present invention includes a reflecting face that reflects light emitted by an emission section emitting light for imaging an ocular fundus of a subject's eye, and that scans the light in a specific direction by changing orientation; a concave mirror face disposed such that light reflected by a reflecting face is incident to the ocular fundus and such that a focal point based on light reflected by the reflecting face is positioned at the subject's eye; and a plurality of light sources that emit fixation target light, which is light indicating a fixation target, in a state facing the ocular fundus via the reflecting face and the mirror face, the plurality of light sources including: a first light source that lights up in a case in which the orientation of the reflecting face is a first orientation causing the light to be emitted onto a first end portion, which is one end portion in the specific direction of the central region of the ocular fundus; and a second light source that lights up in a case in which the orientation of the reflecting face is a second orientation causing the light to be emitted onto a second end portion, which is another end portion in the specific direction of the central region. Accordingly, the ocular fundus examination device enables implementation of presentation of a fixation target corresponding to a widened angle of a region of ocular fundus onto which light is emitted from a light source for imaging the ocular fundus.

In the ocular fundus examination device of the first embodiment, a speed at which the orientation of the reflecting face changes in a case in which the light is scanned back and forth in the specific direction over the central region so as to pass through the first end portion and the second end portion may be no less than a speed at which a lighting-up of the first light source and a lighting-up of the second light source are perceived through the subject's eye by a subject as continuous lighting-up due to an afterimage effect. Accordingly, the ocular fundus examination device according to the second aspect of the present invention enables the subject to see the fixation target without interruption in a case in which the light emitted onto the ocular fundus from the light source for imaging the ocular fundus is emitted onto the central region of the ocular fundus and imaged.

In a variant of either of the ocular fundus examination devices set out above, the plurality of light sources may further include: a third light source that lights up in a case in which the orientation of the reflecting face is a third orientation causing the light to be emitted onto a third end portion, which is one end portion in the specific direction of a peripheral region of the central region; and a fourth light source that lights up in a case in which the orientation of the reflecting face is a fourth orientation causing the light to be emitted onto a fourth end portion, which is another end portion in the specific direction of the peripheral region. Accordingly, the ocular fundus examination device can enable implementation of presentation of a fixation target corresponding to the peripheral region of the central region of the ocular fundus.

Furthermore, in the variant ocular fundus examination device, a speed at which the orientation of the reflecting face changes in a case in which the light is scanned back and forth in the specific direction over the central region and the peripheral region so as to pass through the third end portion and the fourth end portion may be no less than a speed at which the lighting-up of the third light source and the lighting-up of the fourth light source are perceived through the subject's eye by a subject as continuous lighting-up due to an afterimage effect. Accordingly, the ocular fundus examination device may thus enable the subject to see the fixation target without interruption in a case in which the light emitted onto the ocular fundus from the light source for imaging the ocular fundus is emitted onto the peripheral region of the central region of the ocular fundus and imaged.

An ocular fundus examination device according to a second embodiment of the present invention includes a first reflecting face that reflects light emitted by an emission section emitting light for imaging an ocular fundus of a subject's eye, and that scans the light in a specific direction by changing orientation; a concave mirror face disposed such that light reflected by the first reflecting face is incident to the ocular fundus, and such that a focal point based on the light reflected by the first reflecting face is positioned at the subject's eye; a light source that is disposed at a position separated from an optical pathway of the light, and that emits fixation target light, which is light indicating a fixation target; a second reflecting face that is disposed at a position separated from an optical pathway of the light in a case in which the light is emitted onto a peripheral region of a central region of the ocular fundus, that reflects the fixation target light emitted from the light source at a first position, and that is capable of emitting the reflected fixation target light in a state facing the ocular fundus via the mirror face; a moving mechanism that by receiving drive force from a drive source, causes the second reflecting face to move between the first position and a second position separated from an optical pathway of the light in a case in which the light is emitted onto the central region; and a controller configured to control the drive source and the light source such that the second reflecting face is disposed at the first position and the light source is lit up in a case in which the orientation of the first reflecting face is an orientation causing the light to be emitted onto the peripheral region, and such that the second reflecting face is disposed at the second position and the light source is lit up in a case in which the orientation of the first reflecting face is an orientation causing the light to be emitted onto the central region. Accordingly, the ocular fundus examination device according to the second embodiment of the present invention enables implementation of presentation of a fixation target corresponding to a widened angle of a region of ocular fundus onto which light is emitted from a light source for imaging the ocular fundus.

An ocular fundus examination device according to a third embodiment of the present invention includes a first reflecting face that reflects light emitted by an emission section emitting light for imaging an ocular fundus of a subject's eye, and that scans the light in a specific direction by changing orientation; a concave mirror face disposed such that light reflected by the first reflecting face is incident to the ocular fundus, and such that a focal point based on the light reflected by the first reflecting face is positioned at the subject's eye; a light source that is disposed at a position separated from an optical pathway of the light in a case in which the light is emitted onto a peripheral region of a central region of the ocular fundus, and that, in a first position, is capable of emitting fixation target light, which is light indicating a fixation target, in a state facing the ocular fundus via the mirror face; a moving mechanism that by receiving drive force from a drive source, causes the light source to move between the first position and a second position separated from an optical pathway of the light in a case in which the light is emitted onto the central region; and a controller configured to control the drive source and the light source such that the light source is disposed at the first position and the light source is lit up in a case in which the orientation of the first reflecting face is an orientation causing the light to be emitted onto the peripheral region of the central region of the ocular fundus, and such that the light source is disposed at the second position and the light source is lit up in a case in which the orientation of the first reflecting face is an orientation causing the light to be emitted onto the central region. Accordingly, the ocular fundus examination device according to the third embodiment of the present invention enables implementation of presentation of a fixation target corresponding to a widened angle of a region of ocular fundus onto which light is emitted from a light source for imaging the ocular fundus.

An ocular fundus examination device according to a fourth embodiment of the present invention includes a concave mirror face disposed such that light reflected by a reflecting portion that emits light for imaging an ocular fundus of a subject's eye is incident to the ocular fundus, and such that a focal point based on the light is positioned at the subject's eye; a light source that is disposed at a position separated from an optical pathway of the light, and that emits fixation target light, which is light indicating a fixation target; a reflecting face that is disposed at a position separated from an optical pathway of the light in a case in which the light is emitted onto a peripheral region of a central region of the ocular fundus, that reflects the fixation target light emitted from the light source at a first position, and that is capable of emitting the reflected fixation target light in a state facing the ocular fundus via the mirror face; and a moving mechanism that causes the reflecting face to move between the first position and a second position separated from an optical pathway of the light in a case in which the light is emitted onto the central region. Accordingly, the ocular fundus examination device according to the fourth embodiment of the present invention enables implementation of presentation of a fixation target corresponding to a widened angle of a region of ocular fundus onto which light is emitted from a light source for imaging the ocular fundus.

An ocular fundus examination device according to a fifth embodiment of the present invention includes a concave mirror face disposed such that light reflected by a reflecting portion that emits light for imaging an ocular fundus of a subject's eye is incident to the ocular fundus, and such that a focal point based on the light is positioned at the subject's eye; a light source that is disposed at a position separated from an optical pathway of the light in a case in which the light is emitted onto a peripheral region of a central region of the ocular fundus, and that, in a first position, is capable of emitting fixation target light, which is light indicating a fixation target, in a state facing the ocular fundus via a mirror face; and a moving mechanism that causes the light source to move between the first position and a second position separated from an optical pathway of the light in a case in which the light is emitted onto the central region. Accordingly, the ocular fundus examination device according to the fifth embodiment of the present invention enables implementation of presentation of a fixation target corresponding to a widened angle of a region of ocular fundus onto which light is emitted from a light source for imaging the ocular fundus.

An exemplary embodiment of the present invention has an advantageous effect of enabling a fixation target presentation to be achieved corresponding to a widened angle of a region of ocular fundus onto which light is emitted from a light source for imaging the ocular fundus.

In the following exemplary embodiments, "perpendicular" denotes perpendicular with the meaning encompassing error within a permissible range, and "parallel" denotes parallel with the meaning encompassing error within a permissible range. Moreover, in the exemplary embodiments, "facing" denotes facing with the meaning encompassing error within a permissible range. Moreover, "the same" denotes the same with the meaning encompassing error within a permissible range.

In the exemplary embodiments, super luminescent diode is denoted "SLD" for convenience of explanation. Moreover, interface is denoted "I/F" for convenience of explanation. Moreover, red is denoted "R" and green is denoted "G".

First Exemplary Embodiment

As illustrated in FIG. 1, an ocular fundus examination device 10A, as an example of an ophthalmic device according to an embodiment of the present invention, includes a device main body 12 and a controller 13.

The device main body 12 includes an SLO unit 32, an OCT unit 34, and a shared optical system 36. Note that the SLO unit 32 and the OCT unit 34 are examples of an "emission section" according technology disclosed herein.

The ocular fundus examination device 10A includes SLO imaging system functionality, which is functionality for imaging using SLO, and OCT imaging system functionality, which is functionality for imaging using OCT. The SLO imaging system functionality is implemented by the controller 13, the SLO unit 32, and the shared optical system 36. The OCT imaging system functionality is implemented by the controller 13, the OCT unit 34, and the shared optical system 36.

The ocular fundus examination device 10A includes an SLO mode, which is an operation mode that exercises the SLO imaging system functionality, and an OCT mode, which is an operation mode that exercises the OCT imaging system functionality. The SLO mode and the OCT mode are selectively set according to user instructions or sequence control.

The SLO unit 32 includes an emission section 40, a beam splitter 42, a polygon mirror 44, a photo detector 46, and a motor 48, that are employed to generate a two-dimensional image of the surface of the ocular fundus of a subject's eye 38.

The ocular fundus of the subject's eye 38 is simply denoted the "ocular fundus" hereafter for convenience of explanation. Moreover, in a case in which, for example, the ocular fundus examination device 10A is installed on a horizontal surface, a direction perpendicular to the horizontal surface (not illustrated in the drawings) is denoted the "Y direction" for convenience of explanation. Moreover, for example, a direction that is parallel to a horizontal surface and that is the depth direction of the subject's eye 38 positioned in a state in which an anterior segment is facing an eyepiece lens (not illustrated in the drawings) of the ocular fundus examination device 10A, in a case in which the ocular fundus examination device 10A is installed on the horizontal surface, is denoted the "Z direction" hereafter for convenience of explanation. Moreover, a direction perpendicular to both the Y direction and the Z direction is denoted the "X direction" hereafter for convenience of explanation.

The emission section 40 includes a light source 40A and a bandpass filter 40B. The light source 40A is a light source for imaging using SLO, and emits light having a wavelength in a range of from approximately 400 nanometers to approximately 900 nanometers. Light emitted from the light source 40A passes through the bandpass filter 40B such that only light having specific wavelengths is emitted onto the beam splitter 42.

In the present first exemplary embodiment, light emitted from the emission section 40 is broadly split into visible RG light and near-infrared light, which is light having a wavelength in the near-infrared region.

In the present first exemplary embodiment, RG light and near-infrared light are selectively emitted from the emission section 40 by varying the wavelength of the light produced by the light source 40A, and by applying the bandpass filter 40B to the light produced by the light source 40A.

For convenience of explanation, RG light and near-infrared light, serving as the light emitted from the emission section 40, are simply referred to as "SLO light" hereafter in a case in which explanation does not need to distinguish between the two. Moreover, the SLO light is an example of "light for imaging the ocular fundus of a subject's eye" (also referred to as "scanning light") according to technology disclosed herein.

The beam splitter 42 guides the SLO light to the polygon mirror 44 by transmitting the SLO light, and guides first ocular fundus reflected light to the photo detector 46. Here, first ocular fundus reflected light denotes light reflected by the ocular fundus originating from the SLO light. Light reflected by the ocular fundus denotes light that was reflected by the ocular fundus and was then incident to the shared optical system 36.

The polygon mirror 44 sends the SLO light from the beam splitter 42 to the shared optical system 36. Then, as illustrated as an example in FIG. 2, the polygon mirror 44 scans the SLO light in the Y direction by rotating in the arrow A direction on receiving drive force of the motor 48.

The photo detector 46 includes a photo detector 46A and an optical filter 46B. The optical filter 46B is disposed at a position between an optical reception face 46A1 of the photo detector 46A and a reflecting face 42A of the beam splitter 42, and covers an optical reception face 46A1. First ocular fundus reflected light made of near-infrared light and first ocular fundus reflected light made of RG light are selectively made incident to the optical reception face 46A1.

The photo detector 46A generates an SLO image signal, which is an image signal based on the first ocular fundus reflected light that was incident via the optical filter 46B, and outputs the generated SLO image signal.

The OCT unit 34 is employed to generate a tomographic image of the ocular fundus, and includes an SLD 50, an optical coupler 52, a reference light optical system 54, a spectrophotometer 56, a line sensor 58, a V-galvanometer mirror 60, and a motor 62.

The SLD 50 emits low-coherence light. Low-coherence light, for example, denotes light encompassing light in the near-infrared region having a longer wavelength than near-infrared light emitted from the emission section 40 and having a time-wise coherence length of approximately several tens of micrometers.

Low-coherence light emitted from the SLD 50 is fed into the optical coupler 52 via a first optical fiber (not illustrated in the drawings) and is split into reference light and signal light. The reference light is guided to the reference light optical system 54 via a second optical fiber (not illustrated in the drawings), and the signal light is guided to the V-galvanometer mirror 60 via a third optical fiber (not illustrated in the drawings). Note that the signal light is an example of "light for imaging the ocular fundus of a subject's eye" (also referred to as "scanning light") according to technology disclosed herein.

The reference light optical system 54 includes a collimator lens (not illustrated in the drawings), dispersion compensating glass (not illustrated in the drawings), and a reference mirror (not illustrated in the drawings). Reference light is guided to the reference mirror via the collimator lens and the dispersion compensating glass.

The reference mirror returns reference light to the optical coupler 52 via the same optical path by reflecting the reference light. The reference mirror is a movable mirror that can move in the direction of the optical axis of the reference light, and the length of the optical path of the reference light is adjusted by moving the position of the reference mirror on the optical axis. Images of the ocular fundus at different positions in the Z direction can be acquired by moving the reference mirror.

The V-galvanometer mirror 60 sends signal light to the shared optical system 36. Then, as illustrated as an example in FIG. 2, the V-galvanometer mirror 60 scans the signal light in the Y direction by rotationally oscillating in the arrow B direction on receiving drive force of the motor 62.

Moreover, the V-galvanometer mirror 60 guides second ocular fundus reflected light to the optical coupler 52 via a fourth optical fiber. Here, the second ocular fundus reflected light denotes light reflected by the ocular fundus originating from signal light.

The second ocular fundus reflected light guided by the optical coupler 52 is superimposed with the reference light guided from the reference light optical system to the optical coupler 52 by the optical coupler 52 and interference occurs. Interference light obtained due to the interference occurring is spectrally dispersed by the spectrophotometer 56, and the spectrally dispersed interference light is guided to the line sensor 58.

The line sensor 58 generates an OCT image signal, which is an image signal based on incident interference light, and outputs the generated OCT image signal.

The shared optical system 36 includes a dichroic mirror 64, a slit mirror 66 that has an elliptical concave reflecting face, an H-galvanometer mirror 68, an ellipsoid mirror 70, and a motor 72.

The dichroic mirror 64 guides the SLO light to the slit mirror 66 by causing the SLO light from the polygon mirror 44 of the SLO unit 32 to be transmitted, and guides the signal light to the slit mirror 66 by causing the signal light from the V-galvanometer mirror 60 of the OCT unit 34 to be reflected.

For convenience of explanation, signal light and SLO light are denoted "emitted light" or "scanning light" hereafter in a case in which there is no need for the explanation to distinguish between the two.

Figure 2:
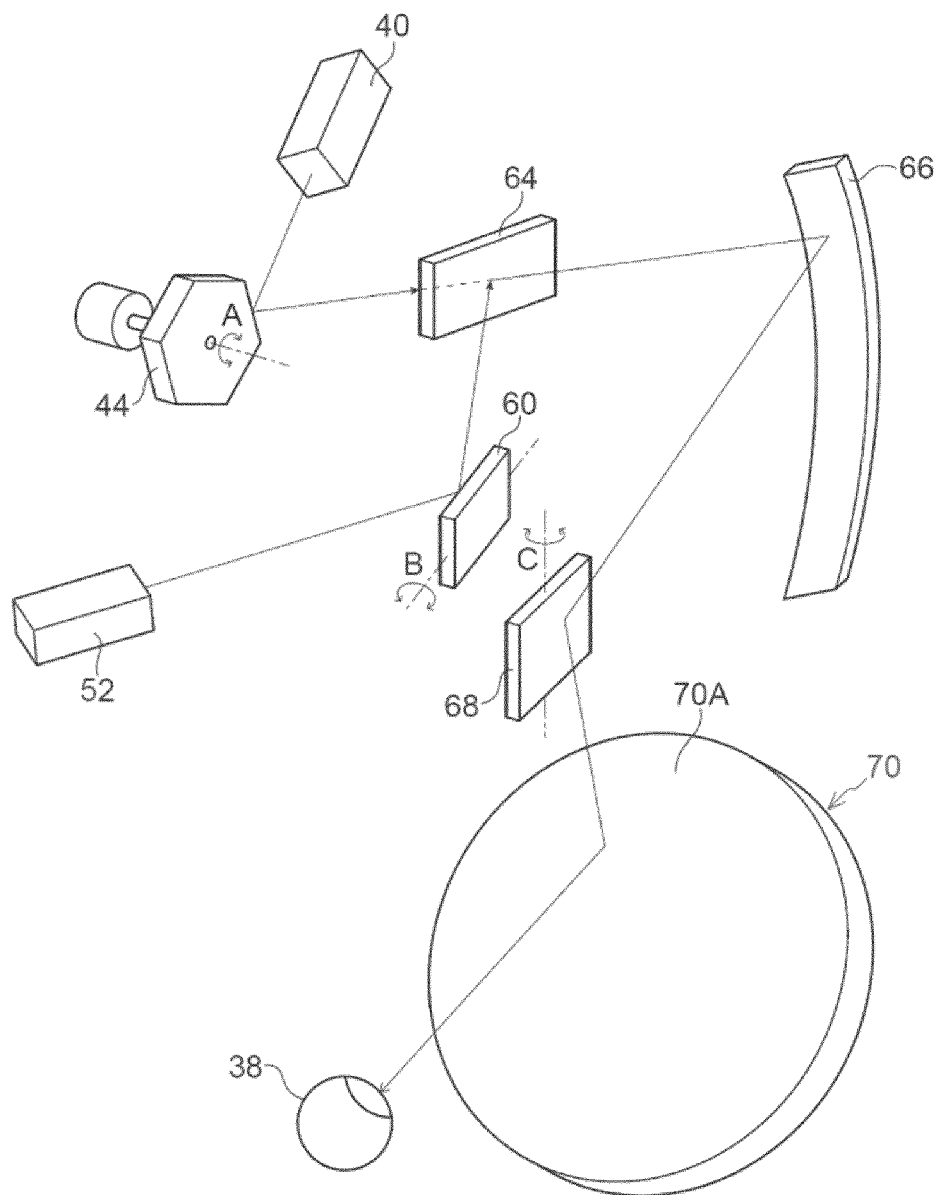
FIG. 2 is a schematic perspective view illustrating an example of a configuration of an optical system that guides light emitted from respective light sources of an imaging system of an ocular fundus examination device to a subject's eye, according to the first to the fourth exemplary embodiment.

The slit mirror 66 reflects incident emitted light toward the H-galvanometer mirror 68. The H-galvanometer mirror 68 reflects and sends the emitted light from the slit mirror 66 to a mirror face 70A of the ellipsoid mirror 70. Then, as illustrated in the example of FIG. 2, the H-galvanometer mirror 68 scans the emitted light in an X direction by rotationally oscillating in the arrow C direction on receiving drive force from the motor 72. Note that the X direction is an example of a "specific direction" according to technology disclosed herein. The mirror face 70A is an example of a "concave mirror face" according to technology disclosed herein.

The ellipsoid mirror 70 guides emitted light to the ocular fundus by reflecting emitted light that was incident to the mirror face 70A. The ellipsoid mirror 70 is disposed such that a focal point based on the emitted light reflected by the mirror face 70A is positioned at the subject's eye 38. In other words, the ellipsoid mirror 70 is disposed such that a focal point thereof is located at the pupil of the subject's eye 38 during use of the ocular fundus examination device 10A. Emitted light guided to the ocular fundus by the ellipsoid mirror 70 is reflected by the ocular fundus. Then, the ocular fundus reflected light is guided to the dichroic mirror 64 in the shared optical system 36, along the same optical path as the emitted light. The dichroic mirror 64 guides the first ocular fundus reflected light to the SLO unit 32 and guides the second ocular fundus reflected light to the OCT unit 34. Basic configuration of an ocular fundus imaging optical system configured by two elliptical faces is similar to the configurations described in PCT application No. PCT/GB94/02465 (WO 95/13012) and PCT application No. PCT/GB2007/002208 (WO 2008/009877), the disclosures of each of which are incorporated herein by reference. Further, the embodiments herein can be combined, both structurally and operationally, with the technically-related systems and methodologies disclosed in, for example, U.S. Pat. No. 7,959,290, US 2015/0216408, US 2014/0327882, US 2013/0135583, and US 2013/0335703, the disclosures of each of which are also incorporated herein by reference.

In the ocular fundus examination device 10A, as illustrated as an example in FIG. 1, a region of the ocular fundus the emitted light is emitted onto is broadly split into a first emitted-onto region α serving as an example of a "fundus central region" according to technology disclosed herein, and a second emitted-onto region β serving as an example of a "peripheral region" according to technology disclosed herein. The emitted light may illuminate the periphery of the retina when it is incident on the eye 38 at an angle greater than ±30 degrees.

First emitted-onto region α denotes, for example, an angle range on the Z direction side of 45° about the center O of the subject's eye 38, in other words, a region spreading out along the circumferential direction of the ocular fundus from the center of the ocular fundus at an angle of 45°, with the center O of the subject's eye 38 as a reference point. Second emitted-onto region β denotes, for example, an angle range on the Z direction side of more than 45° but no more than 200° about the center O of the subject's eye 38, in other words, a region spreading out over an angle range of more than 45° but no more than 200° from the center of the ocular fundus along the circumferential direction of the ocular fundus, with the center O of the subject's eye 38.

The controller 13 controls operation of the device main body 12 by exchanging a variety of information with the device main body 12. Moreover, the controller 13 generates a two-dimensional image indicating an aspect of the surface of the ocular fundus based on the SLO image signal obtained from the photo detector 46A. The controller 13 also generates a tomographic image of the ocular fundus based on the OCT image signal obtained from the line sensor 58.

Note that in this first exemplary embodiment, the two-dimensional image obtained using the SLO unit 32 is broadly split into a chromatic image based on RG light and an achromatic image based on near-infrared light. Moreover, tomographic images obtained using the OCT unit 34 are achromatic images. Two-dimensional images obtained using the SLO unit 32 and the tomographic image obtained using the OCT unit 34 may be displayed as still images, or may be displayed as a live view image.

The controller 13 includes a primary controller 14, an OCT image generator 16, an SLO image generator 18, a reception I/F 20, a reception device 22, a display controller 24, a display 26, a communication I/F 28, and a bus line 30.

The primary controller 14, the OCT image generator 16, the SLO image generator 18, the reception I/F 20, the display controller 24, and the communication I/F 28 are connected to one another by the bus line 30. Accordingly, the primary controller 14 can exchange various items of information with the OCT image generator 16, the SLO image generator 18, the reception I/F 20, the display controller 24, and the communication I/F 28.

The primary controller 14 controls driving of the motors 48, 62, 72 by controlling respective motor drive circuits (not illustrated in the drawings) corresponding to the motors 48, 62, 72 via the communication I/F 28.

Moreover, the primary controller 14 switches between lighting-up and lighting-out the light source 40A, adjusts the amount of light, changes the wavelength of light produced by the light source 40A, and the like, by controlling a light source drive circuit (not illustrated in the drawings) corresponding to the light source 40A via the communication I/F 28.

Moreover, the primary controller 14 switches between lighting-up and lighting-out the SLD 50, adjusts the amount of light, changes the wavelength of light produced by the SLD 50, and the like, by controlling a SLD drive circuit (not illustrated in the drawings) corresponding to the SLD 50 via the communication I/F 28.

Moreover, the primary controller 14 controls operation of the bandpass filter 40B, operation of the optical filter 46B, and operation of the reference mirror of the reference light optical system 54 via the communication I/F 28.

The reception device 22 includes a keyboard, a mouse, a touch panel, or the like, and receives various instructions from a user.

The reception device 22 is connected to the reception I/F 20 and outputs an instruction content signal indicating contents of the received instructions to the reception I/F 20. The primary controller 14 executes processing in accordance with the instruction content signal input from the reception I/F 20.

The display 26 is, for example, an LCD or organic electroluminescence display (OELD). The display 26 is connected to the display controller 24. Under control by the primary controller 14, the display controller 24 controls the display 26 so as to display on the display 26 a two-dimensional image obtained using the SLO unit 32 and a tomographic image obtained using the OCT unit 34, as still images or a live view image. Under control by the primary controller 14, the display controller 24 also displays various screens, such as menu screens, by controlling the display 26.

The communication I/F 28 is connected to an electrical system of a device main body 34, and operates under control by the primary controller 14 to govern exchange of various information between the primary controller 14 and the device main body 34.

The SLO image generator 18 acquires the SLO image signal from the photo detector 46A of the SLO unit 32 via the communication I/F 28, and is a dedicated circuit that performs processing to generate a two-dimensional image based on the acquired SLO image signal.

The SLO image generator 18, for example, outputs each frame of the generated two-dimensional images to the display controller 24 at a specific frame rate of several tens of frames per second. The display controller 24 displays the two-dimensional images input from the SLO image generator 18 on the display 26 as a live view image in accordance with instructions by the primary controller 14. Moreover, the display controller 24 displays the two-dimensional images input from the SLO image generator 18 on the display 26 as still images, in accordance with instructions by the primary controller 14.

The OCT image generator 16 acquires the OCT image signal from the line sensor 58 of the OCT unit 34 via the communication I/F 28, and is a dedicated circuit that performs processing to generate a tomographic image based on the acquired OCT image signal.

The OCT image generator 16, for example, outputs each frame of the generated tomographic images to the display controller 24 at a specific frame rate of several tens of frames per second. The display controller 24 displays the tomographic images input from the OCT image generator 16 on the display 26 as a live view image in accordance with instructions by the primary controller 14. Moreover, the display controller 24 displays the tomographic images input from the OCT image generator 16 on the display 26 as still images, in accordance with instructions by the primary controller 14.

Note that in this first exemplary embodiment, an example is given in which the OCT image generator 16 and the SLO image generator 18 are each implemented by field-programmable gate arrays (FPGA); however, technology disclosed herein is not limited thereto. For example, the OCT image generator 16 and the SLO image generator 18 may each be implemented by a computer that includes a CPU, ROM, and RAM, or may be implemented by an application specific integrated circuit (ASIC). Moreover, the OCT image generator 16 and the SLO image generator 18 may each be implemented by a combination of hardware configuration and software configuration.

Figure 3:
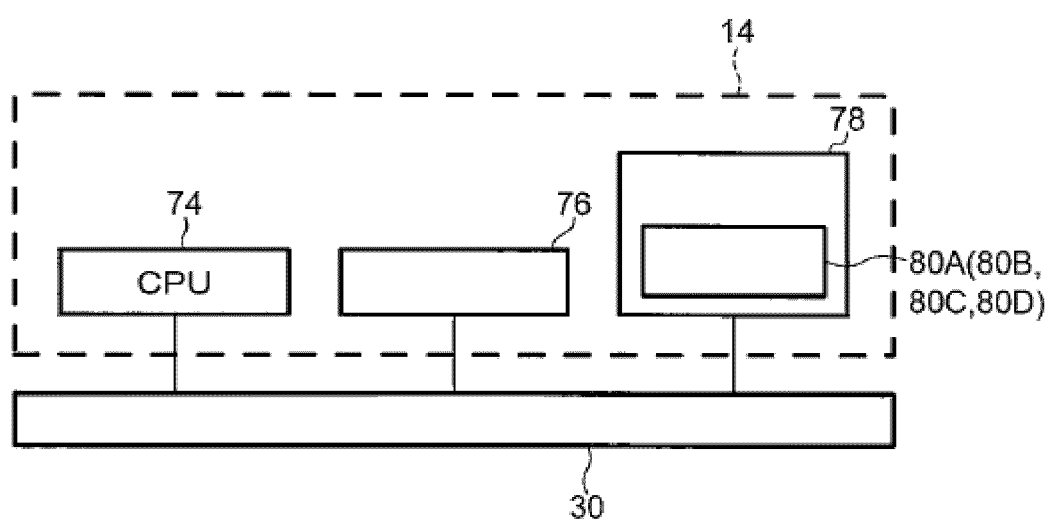
FIG. 3 is a block diagram illustrating an example of a hardware configuration of a primary controller included in an ocular fundus examination device according to the first to the fourth exemplary embodiment.

As illustrated as an example in FIG. 3, the primary controller 14 includes a central processing unit (CPU) 74, a primary storage section 76, and a secondary storage section 78. The CPU 74, the primary storage section 76, and the secondary storage section 78 are connected to one another by the bus line 30.

The CPU 74, which is an example of a "controller" according to technology disclosed herein, controls the ocular fundus examination device 10A overall. The primary storage section 76 is volatile memory employed as a work area or the like when executing various programs. Examples of the primary storage section 76 include random access memory (RAM). The secondary storage section 78 is non-volatile memory storing programs, various parameters, and the like for controlling basic operation of the ocular fundus examination device 10A. Examples of the secondary storage section 78 include electrically erasable programmable read only memory (EEPROM) or flash memory.

The secondary storage section 78 stores a program 80A to be executed by the CPU 74 for implementing fixation target light control processing (see FIG. 8), described later.

The CPU 74 operates as a controller according to technology disclosed herein by reading the program 80A from the secondary storage section 78, expanding the program 80A into the primary storage section 76, and executing the program 80A.

Figure 4:
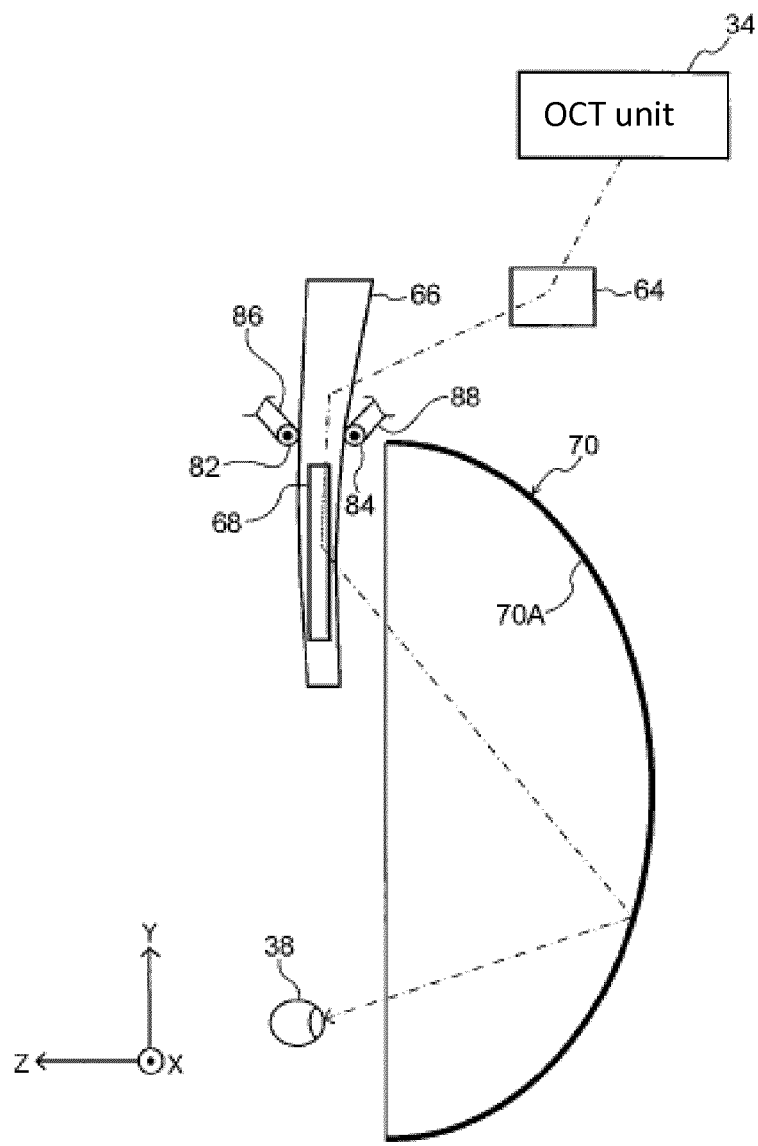
FIG. 4 is a conceptual plan view diagram illustrating a schematic configuration of a dichroic mirror, a slit mirror, an H-galvanometer mirror, an ellipsoid mirror, a first fixation target light source, and a second fixation target light source included in an ocular fundus examination device according to the first exemplary embodiment.

As illustrated as an example in FIG. 4, a first fixation target light source 82 serving as an example of a "first light source" according to technology disclosed herein and a second fixation target light source 84 serving as an example of a "second light source" according to technology disclosed herein are adjacent to the slit mirror 66. The first fixation target light source 82 is fixed to a casing (not illustrated in the drawings) by a frame 86 or the like, and the second fixation target light source 84 is fixed to the casing by a frame 88 or the like.

Here, the first fixation target light source 82 and the second fixation target light source 84 are both light-emitting-diodes (LEDs) that emit fixation target light having the same optical characteristics, such as amount of light, wavelength, and beam diameter, and both are selectively lit up and lit out under control by the controller 13. Note that the fixation target light denotes light indicating a fixation target presented to the subject's eye 38 for fixing the gaze of the subject's eye 38 in a specific position in a case in which the ocular fundus is imaged in the SLO mode and in a case in which the ocular fundus is imaged in the OCT mode. The first fixation target is thus perceived by the subject as being at fixed position and consequently serves to fix the gaze of the subject's eye 38 in a specific direction.

In the present first exemplary embodiment, the fixation target light is broadly split into a first fixation target light emitted from the first fixation target light source 82 and a second fixation target light emitted from the second fixation target light source 84. Note that for convenience of explanation in the present first exemplary embodiment, the first fixation target light and the second fixation target light are simply referred to as the "fixation target light" in a case in which explanation does not distinguish between the two. In FIG. 4 to FIG. 7, the optical path indicated by the single-dotted dashed line is the optical path of the emitted light (or "scanning light"), and the optical path of the fixation target light is indicated by the double-dotted dashed line. As will be explained in the following, the ocular fundus examination device 10A is arranged such that, when the subject's eye 38 is placed at the focal point of the concave mirror 70 during use of the ocular fundus examination device 10A and when either of the fixation target light sources 82 and 84 emits the fixation target light, the fixation target light and the scanning light are simultaneously incident (e.g. at different locations) on the ocular fundus via different optical paths both propagating via the concave mirror face 70A and the focal point, the target fixation light following a predetermined optical path for fixing the gaze of the subject's eye 38.

Figure 5:
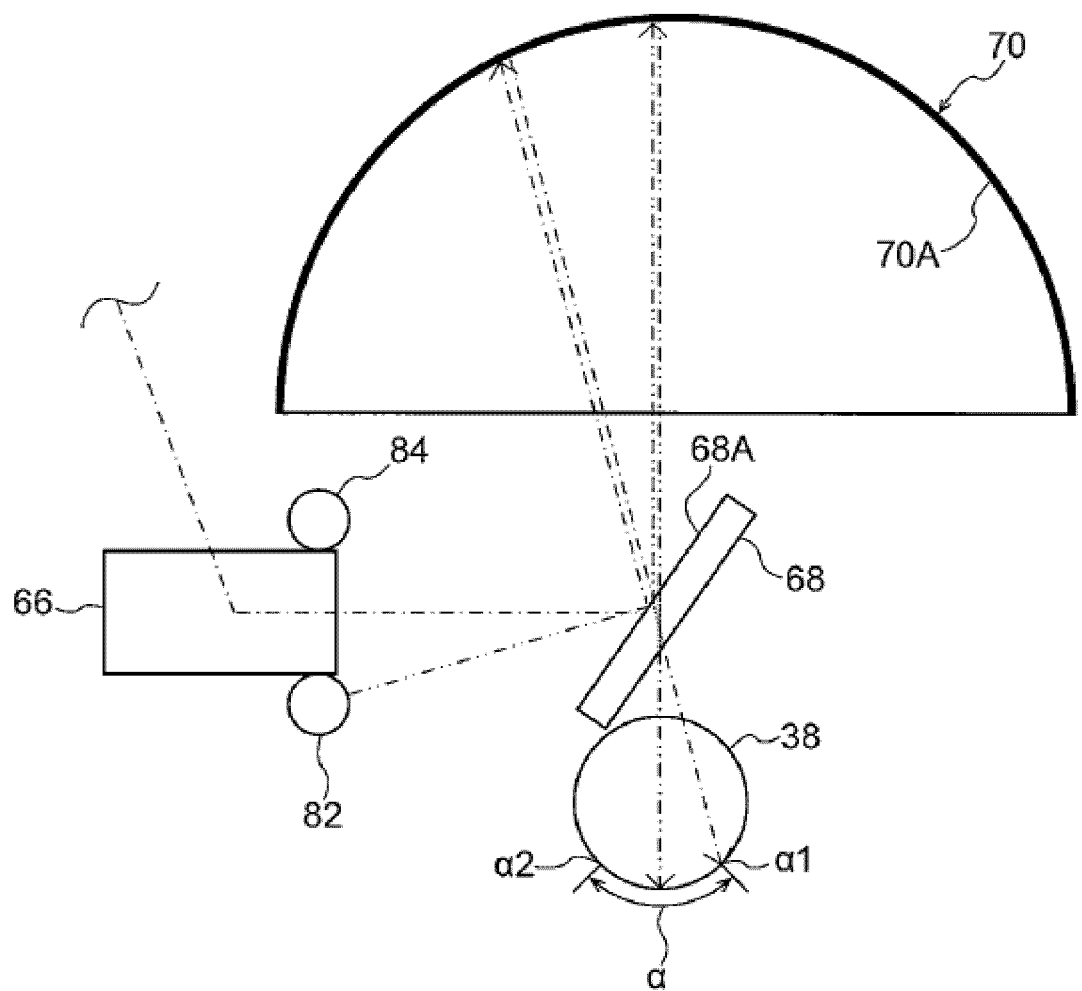
FIG. 5 is a conceptual plan view diagram illustrating an example of relevant configuration according to technology disclosed herein included in an ocular fundus examination device according to the first exemplary embodiment in a state in which a first fixation target light source is lit up.
Figure 6:
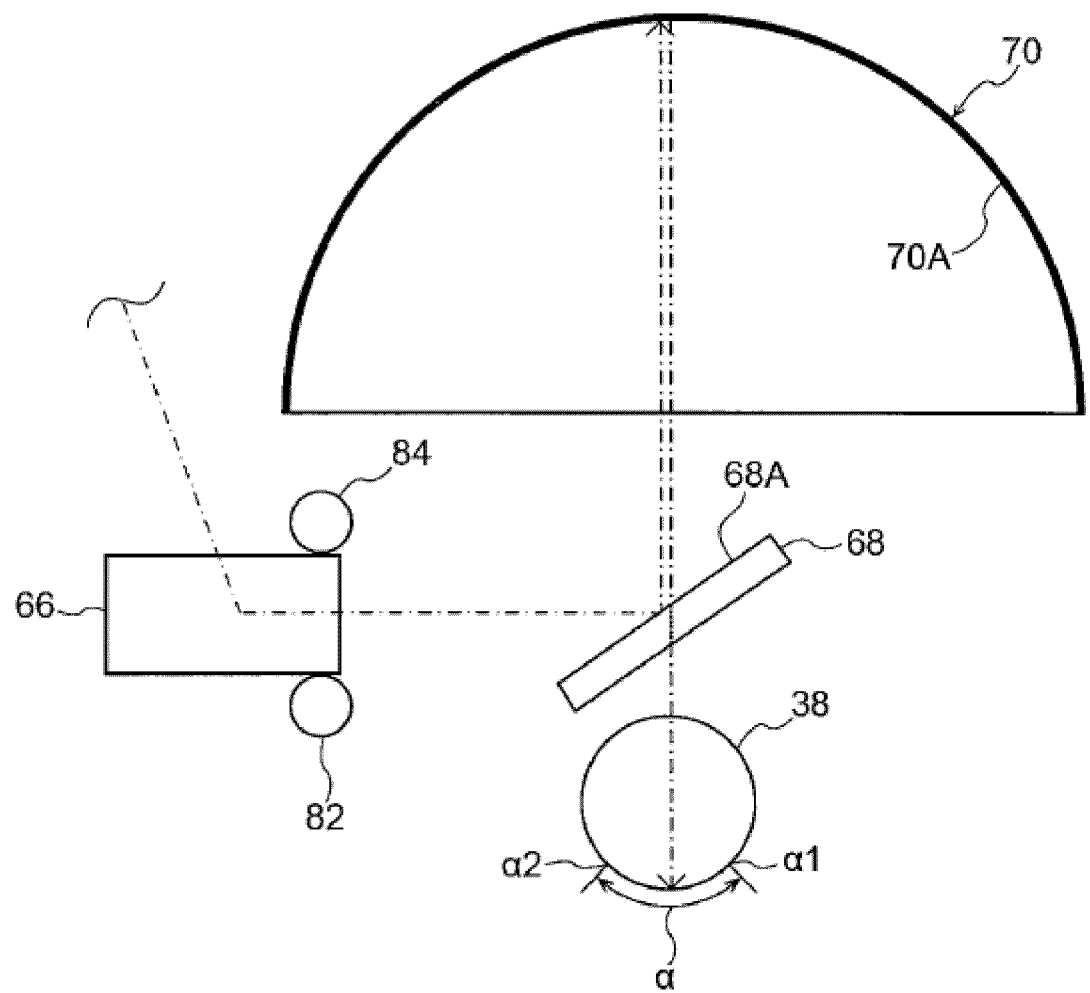
FIG. 6 is a conceptual plan view diagram illustrating an example of relevant configuration according to technology disclosed herein in a state in which a first and a second fixation target light source included in an ocular fundus examination device according to the first exemplary embodiment are extinguished.
Figure 7:
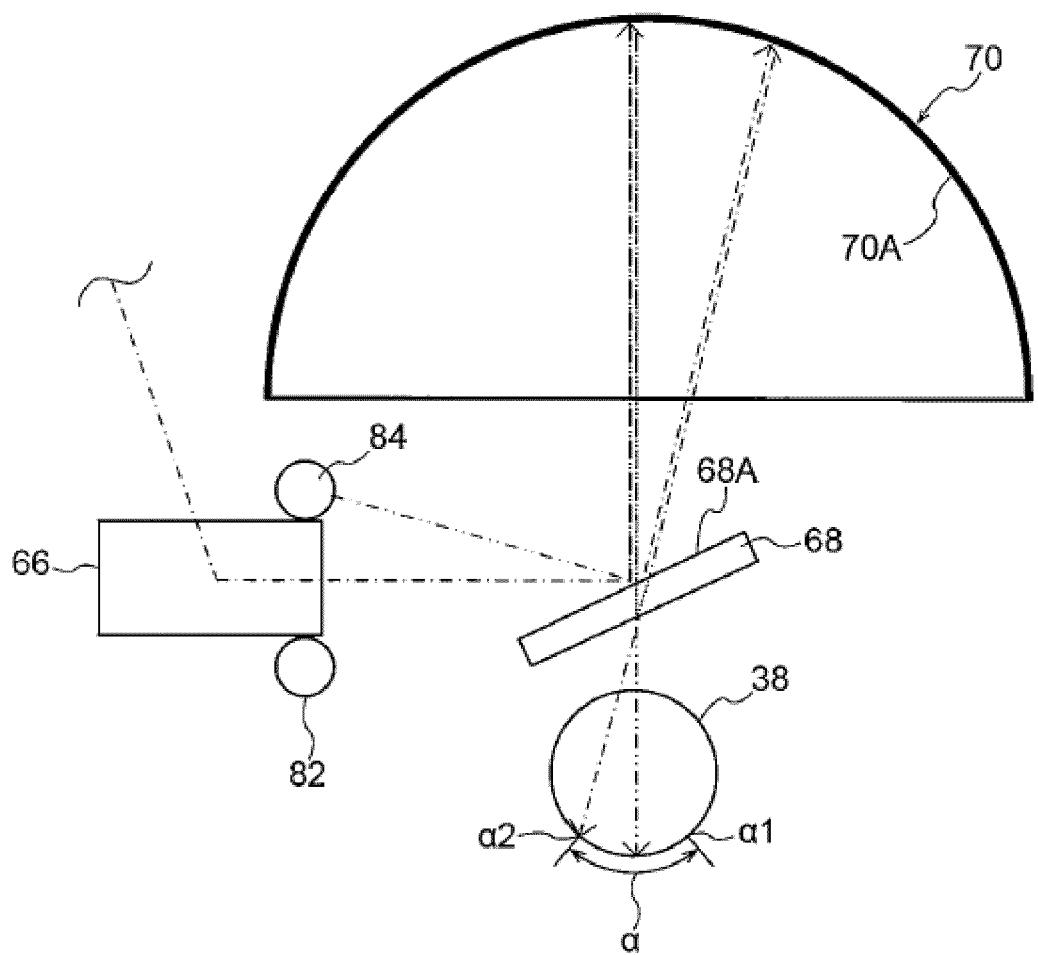
FIG. 7 is a conceptual plan view diagram illustrating an example of relevant configuration according to technology disclosed herein in a state in which a second fixation target light source included in an ocular fundus examination device according to the first exemplary embodiment is lit up.

As illustrated as an example in FIG. 5 to FIG. 7, when signal light is emitted back and forth between a first end portion α1 and a second end portion α2, the revolutions per second of the H-galvanometer mirror 68, namely, the oscillation frequency of the H-galvanometer mirror 68, is, for example, 25 Hz (hertz). Note that here, the first end portion α1 refers to one end portion of the first emitted-onto region α in the X-direction, and the second end portion α2 refers to another end portion of the first emitted-onto region a in the X-direction.

As illustrated as an example in FIG. 5, the first fixation target light source 82 is disposed such that the first fixation target light is emitted onto a central portion (e.g. the fovea) of the first emitted-onto region α in a state facing the ocular fundus in a case in which the orientation of a mirror face 68A of the H-galvanometer mirror 68 is a first orientation. Note that the mirror face 68A of the H-galvanometer mirror 68 is an example of a "reflecting face" and a "first reflecting face" according to technology disclosed herein.

The first fixation target light source 82 is lit up only in a case in which the orientation of the mirror face 68A is the first orientation. Thus, the first fixation target light source 82 is lit up when the orientation of the mirror face 68A is the first orientation, and is not lit up when the mirror face 68A is in all other orientations. Note that here, the first orientation refers, by way of an example, to the orientation of the mirror face 68A in a case in which emitted light is emitted onto the first end portion α1, as illustrated as an example in FIG. 5. The first fixation target light source 82 may more generally be lit up only when the mirror face 68A is orientated in a predetermined orientation, said predetermined orientation being adjustable so as to vary a location on the ocular fundus onto which the fixation target light is emitted.

In a case in which the orientation of the mirror face 68A is the first orientation, the first fixation target light is emitted onto the central portion (e.g. the fovea) of the first emitted-onto region α in a state facing the ocular fundus via the mirror face 68A and the mirror face 70A. Namely, in a case in which the orientation of the mirror face 68A is in the first orientation, the first fixation target light is reflected by the mirror face 68A, the reflected first fixation target light is further reflected by the mirror face 70A, and the first fixation target light reflected by the mirror face 70A arrives at the central portion of the first emitted-onto region α in a state facing the ocular fundus.

As illustrated as an example in FIG. 7, the second fixation target light source 84 is disposed such that the second fixation target light is emitted onto the central portion of the first emitted-onto region α in a state facing the ocular fundus in a case in which the orientation of the mirror face 68A is the second orientation. The second fixation target light source 84 is lit up only in a case in which the orientation of the mirror face 68A is the second orientation. Thus, the second fixation target light source 84 is lit up when the orientation of the mirror face 68A is the second orientation, and is not lit up when the mirror face 68A is in any orientation other than the second orientation. Note that here, the second orientation refers, by way of an example, to the orientation of the mirror face 68A in a case in which the emitted light is emitted onto the second end portion α2, as illustrated as an example in FIG. 7. The second fixation target light source 84 may more generally be lit up only when the mirror face 68A is orientated in a predetermined orientation, said predetermined orientation being adjustable so as to vary a location on the ocular fundus onto which the fixation target light is emitted.

In a case in which the orientation of the mirror face 68A is the second orientation, the second fixation target light is emitted onto the central portion of the first emitted-onto region α in a state facing the ocular fundus via the mirror face 68A and the mirror face 70A. Namely, in a case in which the orientation of the mirror face 68A is in the second orientation, the second fixation target light is reflected by the mirror face 68A, the reflected second fixation target light is further reflected by the mirror face 70A, and the second fixation target light reflected by the mirror face 70A arrives at the central portion of the first emitted-onto region α in a state facing the ocular fundus.

In a case in which, as illustrated as an example in FIG. 6, the orientation of the mirror face 68A is neither the first orientation nor the second orientation, namely, in a case in which the emitted light is not emitted onto the first end portion α1 or the second end portion α2, the first fixation target light source 82 and the second fixation target light source 84 are lit out. Note that in the example illustrated in FIG. 6, the signal light (scanning light) is illustrated in a state emitted onto the central portion of the first emitted-onto region α.

Note that in the present first exemplary embodiment, as described above, the lighting-up of the first fixation target light source 82 and the lighting-up of the second fixation target light source 84 can be caused to be perceived through the subject's eye 38 by the subject as a continuous lighting-up due to an afterimage effect since the H-galvanometer mirror 68 rotationally operates at 25 Hz. Thus, although an example is given regarding a case in which the H-galvanometer mirror 68 rotationally operates at 25 Hz in the OCT mode in the present first exemplary embodiment, technology disclosed herein is not limited thereto. For example, it is sufficient for the speed of orientation change of the H-galvanometer mirror 68 to be a speed at which the lighting-up of the first fixation target light source 82 and the lighting-up of the second fixation target light source 84 are caused to be perceived through the subject's eye 38 by the subject as a continuous lighting-up due to the afterimage effect. However, regardless of the speed of orientation change of the H-galvanometer mirror 68, the first and second fixation target light sources 82 and 84 are controlled by the CPU 74 to light up and emit the respective first and second fixation target lights onto the subject's ocular fundus only at the first and second orientations of the H-galvanometer mirror 68 described above, respectively, such that the subject perceives the fixation target as being fixed in one place. The fixation target may appear to the subject to either flash or to be continuously lit up (depending on the speed of orientation change of the H-galvanometer mirror 68) but will in both cases appear to be fixed.

Figure 8:
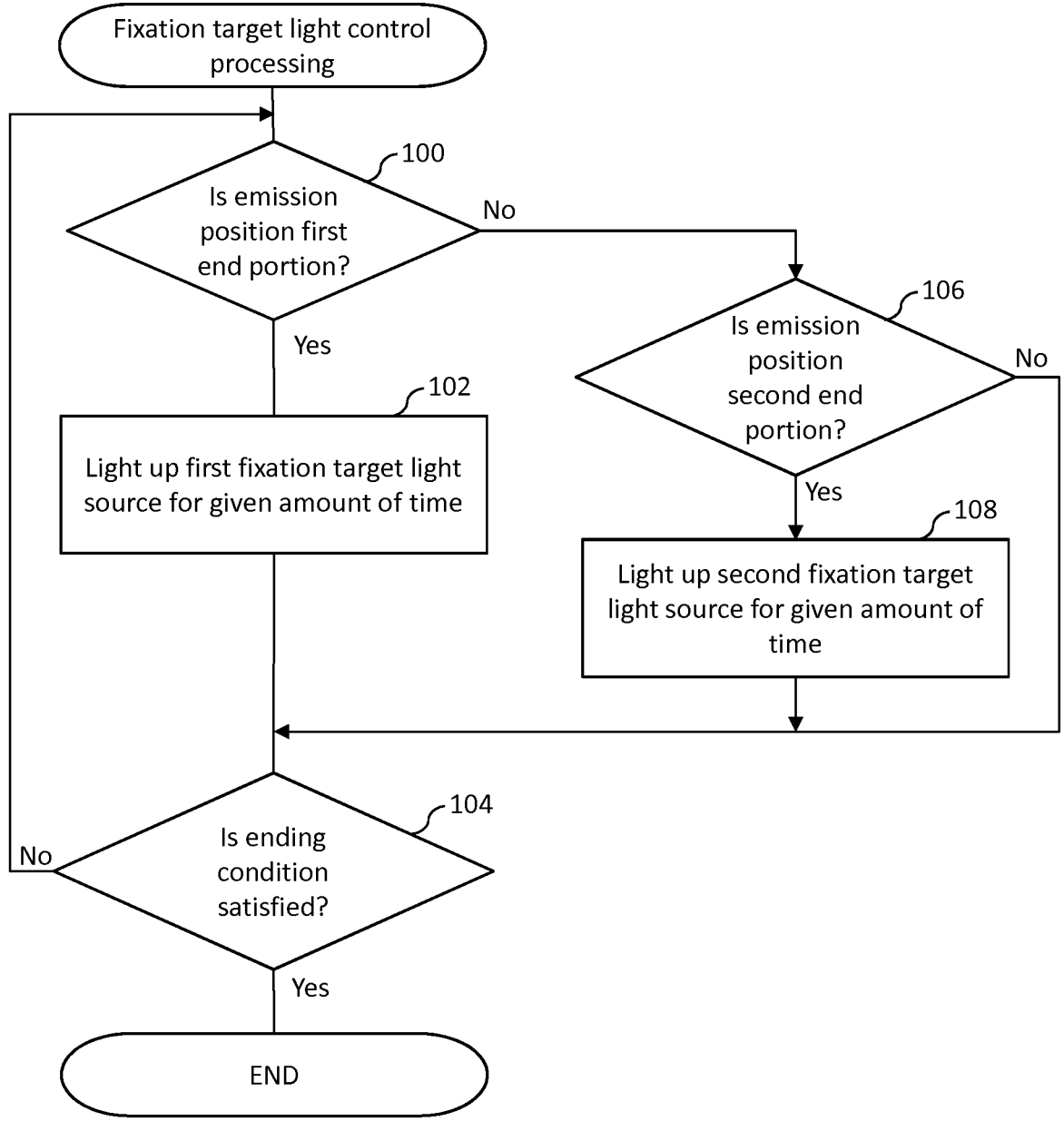
FIG. 8 is a flowchart illustrating an example of a flow of fixation target light control processing according to the first exemplary embodiment.

Next, explanation follows, with reference to FIG. 8, regarding the fixation target light control processing executed by the CPU 74 following the program 80A in a case in which the ocular fundus is imaged in the OCT mode, as operation of a portion of the ocular fundus examination device 10A according to technology disclosed herein.

In the fixation target light control processing illustrated in FIG. 8, at step 100, the CPU 74 determines whether or not the position on the ocular fundus the signal light is emitted onto is the first end portion α1. At step 100, in a case in which the position on the ocular fundus the signal light is emitted onto is the first end portion α1, affirmative determination is made and processing transitions to step 102. At step 100, in a case in which the position on the ocular fundus the signal light is emitted onto is not the first end portion α1, negative determination is made and processing transitions to step 106.

At step 102, the CPU 74 lights up the first fixation target light source 82 for a given amount of time, and then processing transitions to step 104. Note that at step 102, the given amount of time refers to a minimum amount of time needed for lighting-up the first fixation target light source 82. It is sufficient for the minimum amount of time needed for lighting-up the first fixation target light source 82 to be a predetermined amount of time enabling perception thereof by the subject through the subject's eye 38 based on a result of tests using a real device or a computer simulation or the like.

At step 106, the CPU 74 determines whether or not the position on the ocular fundus the signal light is emitted onto is the second end portion α2. At step 106, in a case in which the position on the ocular fundus the signal light is emitted-onto is the second end portion α2, affirmative determination is made and processing transitions to step 108. At step 106, in a case in which the position on the ocular fundus the signal light is emitted onto is not the second end portion α2, negative determination is made and processing transitions to step 104.

At step 106, the CPU 74 illuminates the second fixation target light source 84 for a given amount of time (for example, the same amount of time as the amount of lighting-up time of the first fixation target light source 82), and then processing transitions to step 104. Note that at the present step 106, the given amount of time refers to the minimum amount of time needed for lighting-up of the second fixation target light source 84. It is sufficient for the minimum amount of time needed for lighting-up the second fixation target light source 84 to be a predetermined amount of time enabling perception thereof by the subject through the subject's eye 38 based on a result of tests using a real device or a computer simulation or the like.

At step 104, the CPU 74 determines whether or not a condition for ending the fixation target light control processing has been satisfied. Note that hereafter, the condition for ending the fixation target light control processing is simply referred to as the "ending condition" for convenience of explanation.

Here, examples of the ending condition include a condition that an instruction to end control of the fixation target light control processing or an instruction to end the OCT mode has been received by the reception device 22, and a condition that acquisition of a tomographic image with a specified range has ended under the OCT mode.

At step 104, in a case in which the ending condition is not satisfied, negative determination is made and processing transitions to step 100. At step 104, in a case in which the ending condition is satisfied, affirmative determination is made and the present fixation target light control processing ends.

As explained above, the ocular fundus examination device 10A includes the first fixation target light source 82 that lights up in a case in which the orientation of the mirror face 68A is the first orientation, and the second fixation target light source 84 that illuminates in a case in which the orientation of the mirror face 68A is the second orientation. More particularly, the first fixation target light source 82 lights up for a predetermined amount of time (e.g. a minimum amount of time needed for lighting-up the first fixation target light source 82 that enables the first fixation target light to be perceived by the subject, the minimum amount of time being determined, e.g. through tests using a real device or a computer simulation or the like) only when the orientation of the mirror face 68A reaches the first orientation, and the second fixation target light source 84 lights up for the predetermined amount of time only when the orientation of the mirror face 68A reaches the second orientation. Accordingly, according to the ocular fundus examination device 10A, presentation of a fixation target corresponding to the first emitted-onto region α can be achieved.

Moreover, in the ocular fundus examination device 10A, the speed of the change in the orientation of the mirror face 68A is a speed causing the lighting-up of the first fixation target light source 82 and the lighting-up of the second fixation target light source 84 to be perceived through the subject's eye 38 by the subject as a continuous lighting-up due to the afterimage effect. Accordingly, according to the ocular fundus examination device 10A, in a case in which the emitted light (the signal light here as an example) is emitted onto the first emitted-onto region α to capture an image, the fixation target can be seen by the subject at a fixed position without interruption.

Second Exemplary Embodiment

In the first exemplary embodiment above, an example was given of a case in which a fixation target was presented to the subject using two fixation target light sources: the first fixation target light source 82 and the second fixation target light source 84. However, the number of fixation target light sources is not limited to two, and single fixation target light source or more than two fixation target light sources may alternatively be provided. In all cases, the source(s) of the fixation target light is/are different to the source(s) of the scanning light, namely the SOL unit 32 and the OCT unit 34 in the present embodiment. In the present second exemplary embodiment, explanation follows regarding a case in which a fixation target is presented to a subject using four fixation target light sources.

Note that in the present second exemplary embodiment, the same reference numerals are allocated to configuration elements that are the same as the configuration elements explained in the first exemplary embodiment above, and explanation thereof is omitted. Explanation primarily focuses on the portions that differ from the first exemplary embodiment above.

Figure 9:
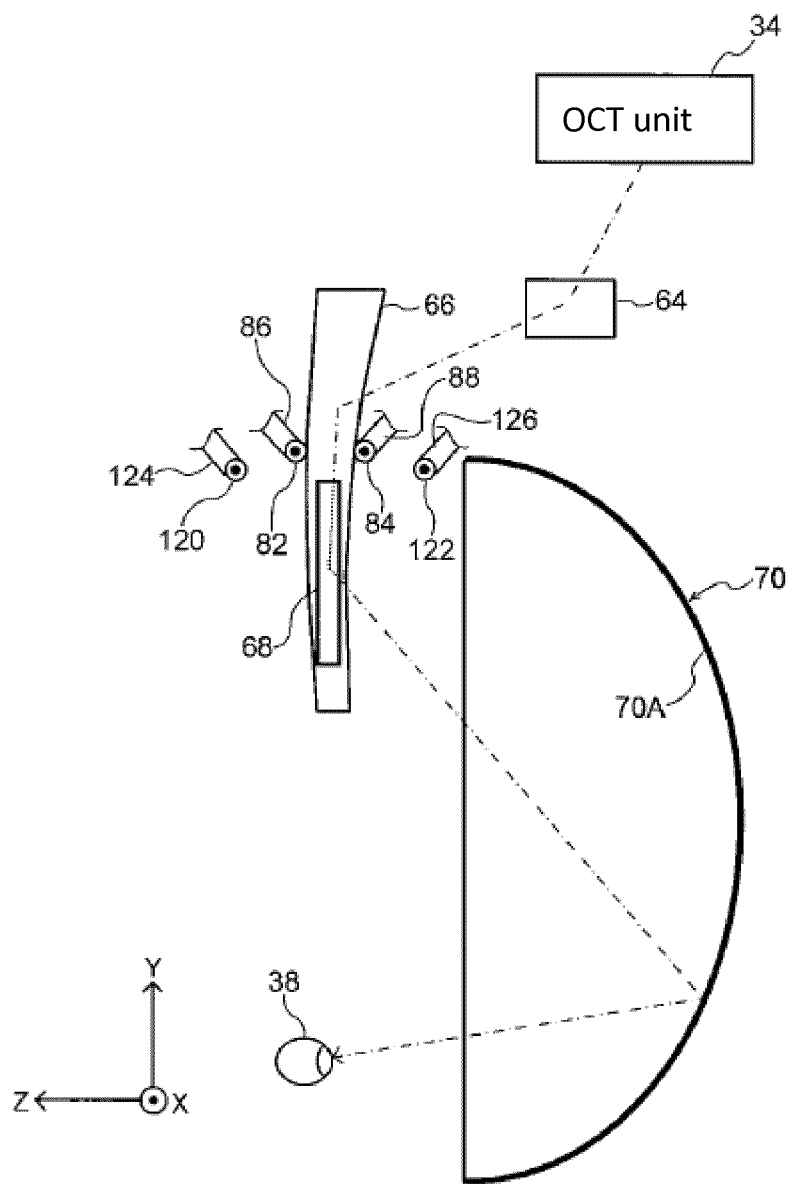
FIG. 9 is a conceptual plan view diagram illustrating a schematic configuration of a dichroic mirror, a slit mirror, an H-galvanometer mirror, an ellipsoid mirror, and a first to a fourth fixation target light source included in an ocular fundus examination device according to the second exemplary embodiment.

The ocular fundus examination device 10B according to present the second exemplary embodiment (see FIG. 1) differs from the ocular fundus examination device 10A explained in the first exemplary embodiment above in that the ocular fundus examination device 10B includes a third fixation target light source 120, a fourth fixation target light source 122, and frames 124, 126, as illustrated as an example in FIG. 9.

Moreover, the ocular fundus examination device 10B differs from the ocular fundus examination device 10A in that the secondary storage section 78 stores a program 80B instead of the program 80A, as illustrated as an example in FIG. 3.

The third fixation target light source 120 is an example of a "third light source" according to technology disclosed herein, and the fourth fixation target light source 122 is an example of a "fourth light source" according to technology disclosed herein.

As illustrated as an example in FIG. 9, the third fixation target light source 120 and the fourth fixation target light source 122 are disposed at locations that face each other in the Z direction across the slit mirror 66, and the fourth fixation target light source 122 is disposed further toward the mirror face 70A side than the third fixation target light source 120.

The third fixation target light source 120 is disposed adjacent to the first fixation target light source 82, and is disposed at a location further separated from the mirror face 70A in the Z direction than the first fixation target light source 82. Moreover, the third fixation target light source 120 is fixed to a casing by the frame 124 or the like.

The fourth fixation target light source 122 is disposed adjacent to the second fixation target light source 84, and is disposed at a location nearer to the mirror face 70A in the Z direction than the second fixation target light source 84. Moreover, the fourth fixation target light source 122 is fixed to a casing by the frame 126 or the like.

Here, the third fixation target light source 120 and the fourth fixation target light source 122 are both LEDs that emit fixation target light having the same optical characteristics, such as amount of light, wavelength, and bean diameter, as the first fixation target light source 82 and the second fixation target light source 84. Moreover, the third fixation target light source 120 and the fourth fixation target light source 122 are both selectively lit up and lit out under control by the controller 13.

In the present second exemplary embodiment, the fixation target light is broadly split into the first fixation target light, the second fixation target light, a third fixation target light emitted from the third fixation target light source 120, and a fourth fixation target light emitted from the fourth fixation target light source 122. Note that for convenience of explanation in the present second exemplary embodiment, the first to the fourth fixation target lights are simply referred to as the "fixation target light" in a case in which explanation does not distinguish between these. Moreover, in FIG. 9 to FIG. 11, the optical path indicated by the single-dotted dashed line is the optical path of the emitted light, and the optical path of the fixation target light is indicated by the double-dotted dashed line.

Figure 10:
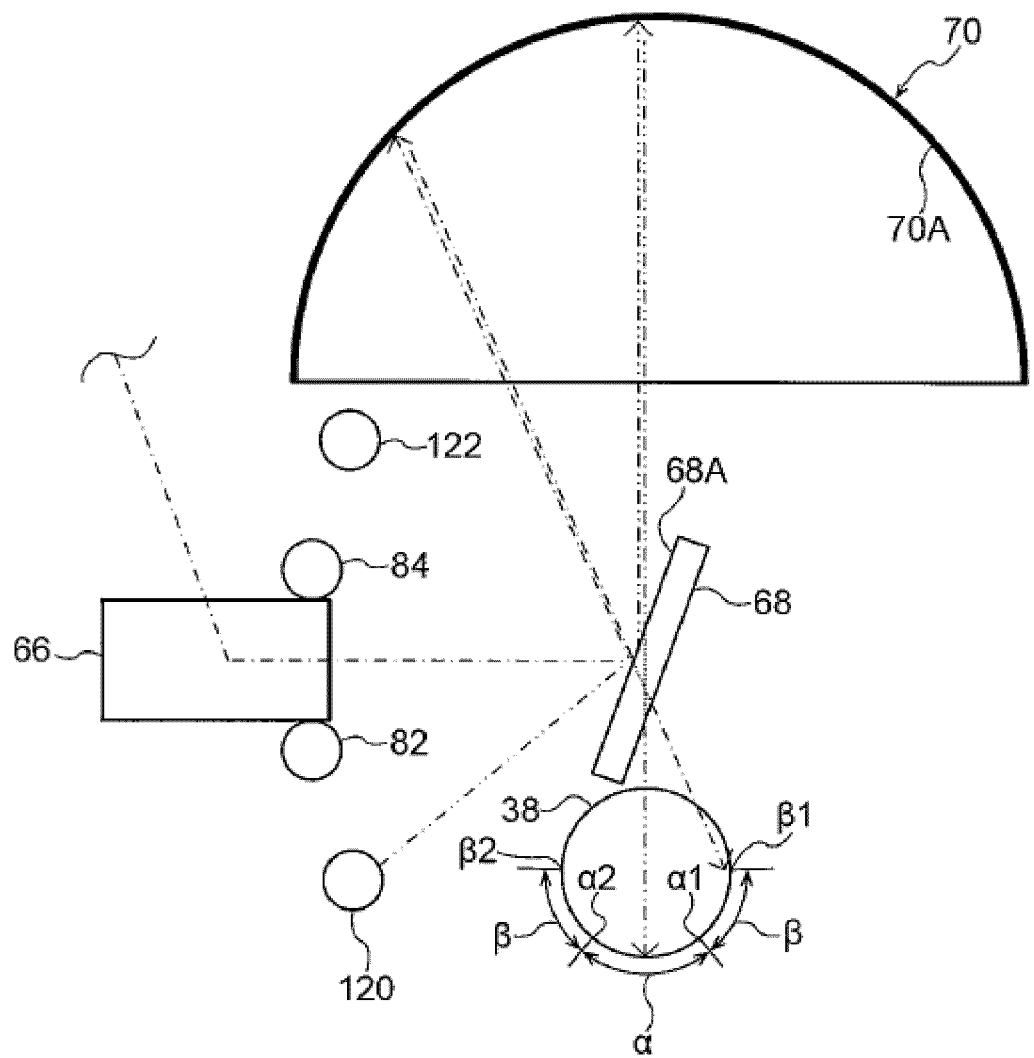
FIG. 10 is a conceptual plan view diagram illustrating an example of relevant configuration according to technology disclosed herein in a state in which a third fixation target light source included in an ocular fundus examination device according to the second exemplary embodiment is lit up.
Figure 11:
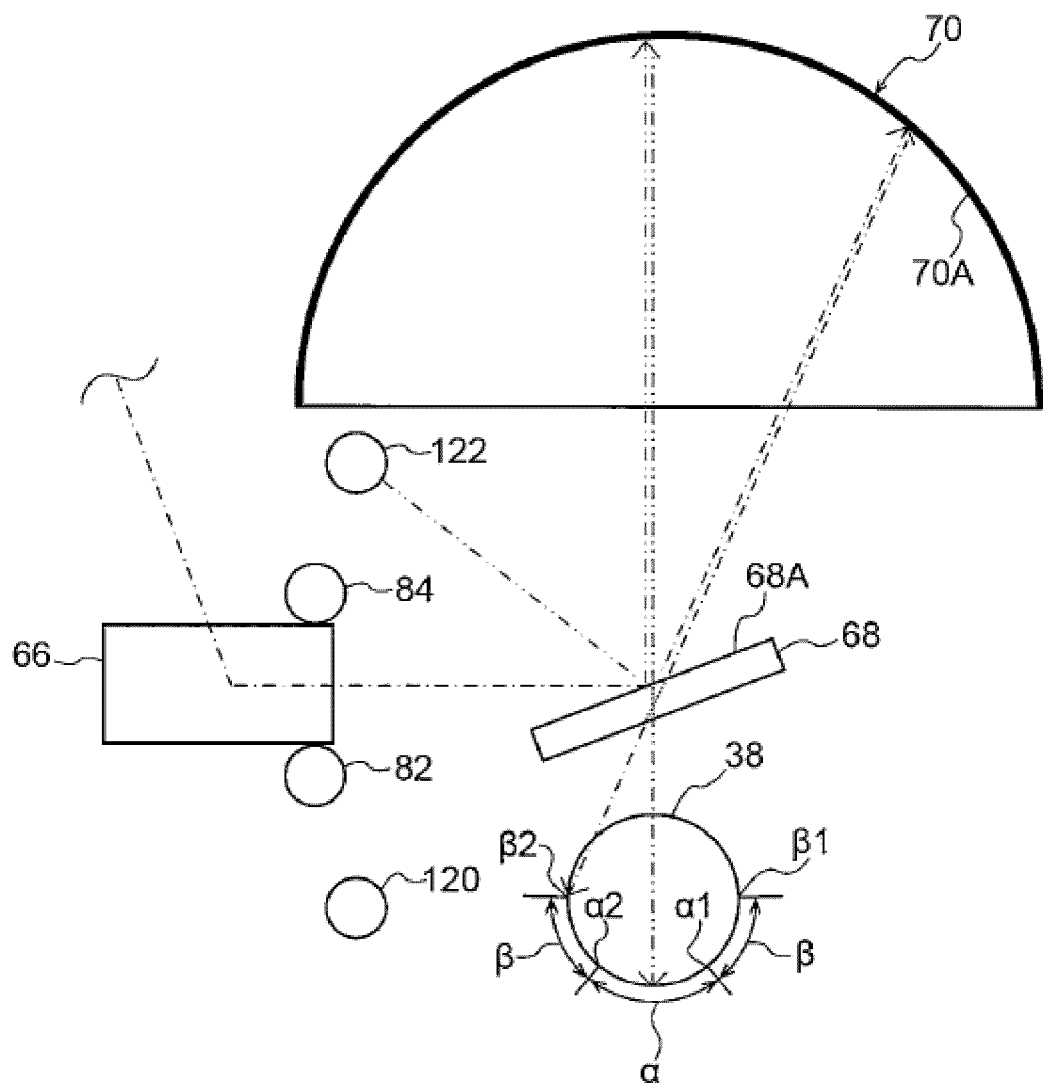
FIG. 11 is a conceptual plan view diagram illustrating an example of relevant configuration according to technology disclosed herein in a state in which a fourth fixation target light source included in an ocular fundus examination device according to the second exemplary embodiment is lit up.

In a case in which signal light is emitted back and forth between a third end portion β1 and a fourth end portion β2 as illustrated as an example in FIG. 10 and FIG. 11, the oscillation frequency of the H-galvanometer mirror 68 is, for example, 25 Hz (hertz). Note that here, the third end portion β1 refers, by way of an example, to one outermost end portion of the second emitted-onto region β in the X-direction, and the fourth end portion β2 refers, by way of an example, to another outermost end portion of the second emitted-onto region β in the X-direction.

As illustrated as an example in FIG. 10, the third fixation target light source 120 is disposed such that the third fixation target light is emitted onto the central portion of the first emitted-onto region α in a state facing the ocular fundus in a case in which the orientation of the mirror face 68A of the H-galvanometer mirror 68 is the third orientation. The third fixation target light source 120 is lit up only in a case in which the orientation of the mirror face 68A is the third orientation. Thus, the third fixation target light source 120 is lit up when the orientation of the mirror face 68A is the third orientation, and is not lit up when the mirror face 68A is in all other orientations. Note that here, the third orientation refers, by way of an example, to the orientation of the mirror face 68A in a case in which the emitted light is emitted onto the third end portion β1, as illustrated as an example in FIG. 10. The third fixation target light source 120 may more generally be lit up only when the mirror face 68A is orientated in a predetermined orientation, said predetermined orientation being adjustable so as to vary a location on the ocular fundus onto which the fixation target light is emitted.

In a case in which the orientation of the mirror face 68A is the third orientation, the third fixation target light is emitted onto the central portion of the first emitted-onto region α in a state facing the ocular fundus via the mirror face 68A and the mirror face 70A. Namely, in a case in which the orientation of the mirror face 68A is in the third orientation, the third fixation target light is reflected by the mirror face 68A, the reflected third fixation target light is further reflected by the mirror face 70A, and the third fixation target light reflected by the mirror face 70A arrives at the central portion of the first emitted-onto region α in a state facing the ocular fundus.

As illustrated as an example in FIG. 11, the fourth fixation target light source 122 is disposed such that the fourth fixation target light is emitted onto the central portion of the first emitted-onto region α in a state facing the ocular fundus in a case in which the orientation of the mirror face 68A is the fourth orientation. The fourth fixation target light source 122 is lit up only in a case in which the orientation of the mirror face 68A is the fourth orientation. Thus, the fourth fixation target light source 122 is lit up when the orientation of the mirror face 68A is the fourth orientation, and is not lit up when the mirror face 68A is in all other orientations. Note that here, the fourth orientation refers to the orientation of the mirror face 68A in a case in which the emitted light is emitted onto the fourth end portion β2, as illustrated as an example in FIG. 11. The fourth fixation target light source 122 may more generally be lit up only when the mirror face 68A is orientated in a predetermined orientation, said predetermined orientation being adjustable so as to vary a location on the ocular fundus onto which the fixation target light is emitted.

In a case in which the orientation of the mirror face 68A is the fourth orientation, the fourth fixation target light is emitted onto the central portion of the first emitted-onto region α in a state facing the ocular fundus via the mirror face 68A and the mirror face 70A. Namely, in a case in which the orientation of the mirror face 68A is in the fourth orientation, the fourth fixation target light is reflected by the mirror face 68A, the reflected fourth fixation target light is further reflected by the mirror face 70A, and the fourth fixation target light reflected by the mirror face 70A arrives at the central portion of the first emitted-onto region α in a state facing the ocular fundus.

Note that in a case in which the orientation of the mirror face 68A is neither the third orientation nor the fourth orientation, namely, in a case in which the emitted light is not emitted onto the third end portion β1 or the fourth end portion β2, the third fixation target light source 120 and the fourth fixation target light source 122 are lit out.

Note that in the present second exemplary embodiment, as described above, the lighting-up of the third fixation target light source 120 and the lighting-up of the fourth fixation target light source 122 can be caused to be perceived through the subject's eye 38 by the subject as a continuous lighting-up due to the afterimage effect since the H-galvanometer mirror 68 rotationally operates at 25 Hz. Although an example is given regarding a case in which the H-galvanometer mirror 68 rotationally operates at 25 Hz in the OCT mode in the present second exemplary embodiment, technology disclosed herein is not limited thereto. For example, it is sufficient for the speed of orientation change of the H-galvanometer mirror 68 to be a speed at which the lighting-up of the third fixation target light source 120 and the lighting-up of the fourth fixation target light source 122 are caused to be perceived through the subject's eye 38 by the subject as a continuous lighting-up due to the afterimage effect. However, regardless of the speed of orientation change of the H-galvanometer mirror 68, the third and fourth fixation target light sources 120 and 122 are controlled by the CPU 74 to light up and emit the respective third and fourth fixation target lights onto the subject's retina only at the third and fourth orientations of the H-galvanometer mirror 68 described above, respectively, such that the subject perceives the fixation target as being fixed in one place.

Figure 12:
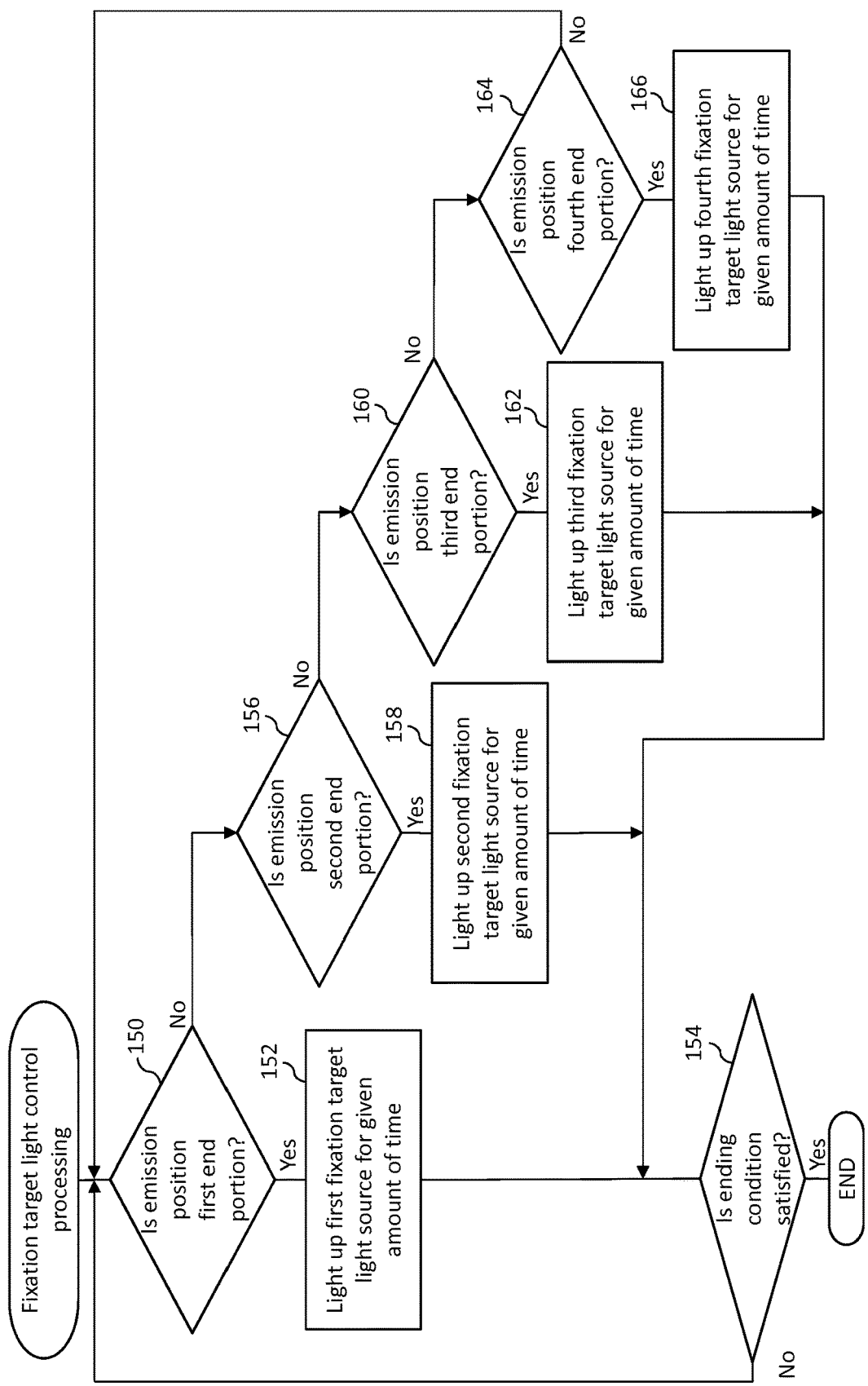
FIG. 12 is a flowchart illustrating an example of a flow of fixation target light control processing according to the second exemplary embodiment.

Next, explanation follows, with reference to FIG. 12, regarding the fixation target light control processing executed by the CPU 74 following the program 80B in a case in which the ocular fundus is imaged in the OCT mode, as operation of a portion of the ocular fundus examination device 10B according to technology disclosed herein.

In the fixation target light control processing illustrated in FIG. 12, at step 150, the CPU 74 determines whether or not the position on the ocular fundus the signal light is emitted onto is the first end portion α1. At step 150, in a case in which the position on the ocular fundus the signal light is emitted onto is the first end portion α1, affirmative determination is made and processing transitions to step 152. At step 150, in a case in which the position on the ocular fundus the signal light is emitted onto is not the first end portion α1, negative determination is made and processing transitions to step 156.

At step 152, the CPU 74 lights up the first fixation target light source 82 for a given amount of time (for example, for the same amount of lighting-up time as the first fixation target light source 82 explained in the first exemplary embodiment above) and then processing transitions to step 154.

At step 156, the CPU 74 determines whether or not the position on the ocular fundus the signal light is emitted onto is the second end portion α2. At step 156, in a case in which the position on the ocular fundus the signal light is emitted onto is the second end portion α2, affirmative determination is made and processing transitions to step 158. At step 156, in a case in which the position on the ocular fundus the signal light is emitted onto is not the second end portion α2, negative determination is made and processing transitions to step 160.

At step 158, the CPU 74 lights up the second fixation target light source 84 for a given amount of time (for example, the same amount of lighting-up time as the first fixation target light source 82) and then processing transitions to step 154.

At step 160, the CPU 74 determines whether or not the position on the ocular fundus the signal light is emitted onto is the third end portion β1. At step 160, in a case in which the position on the ocular fundus the signal light is emitted onto is the third end portion β1, affirmative determination is made and processing transitions to step 162. At step 160, in a case in which the position on the ocular fundus the signal light is emitted onto is not the third end portion β1, negative determination is made and processing transitions to step 164.

At step 162, the CPU 74 lights up the third fixation target light source 120 for a given amount of time (for example, the same amount of lighting-up time as the first fixation target light source 82) and then processing transitions to step 154.

At step 164, the CPU 74 determines whether or not the position on the ocular fundus the signal light is emitted onto is the fourth end portion β2. At step 164, in a case in which the position on the ocular fundus the signal light is emitted onto is the fourth end portion β2, affirmative determination is made and processing transitions to step 166. At step 164, in a case in which the position on the ocular fundus the signal light is emitted onto is not the fourth end portion β2, negative determination is made and processing transitions to step 150.

At step 166, the CPU 74 lights up the fourth fixation target light source 122 for a given amount of time (for example, the same amount of lighting-up time as the first fixation target light source 82) and then processing transitions to step 154.

At step 154, the CPU 74 determines whether or not the ending condition has been satisfied. At step 154, in a case in which the ending condition is not satisfied, negative determination is made and processing transitions to step 150. At step 154, in a case in which the ending condition has been satisfied, affirmative determination is made and the present fixation target light control processing ends.

As explained above, the ocular fundus examination device 10B includes the third fixation target light source 120 that lights up in a case in which the orientation of the mirror face 68A is the third orientation, and the fourth fixation target light source 122 that lights up in a case in which the orientation of the mirror face 68A is the fourth orientation. Accordingly, according to the ocular fundus examination device 10B, presentation of a fixation target corresponding to the second emitted-onto region β can be achieved.

Moreover, in the ocular fundus examination device 10B, the speed of the change in the orientation of the mirror face 68A is a speed that causes the lighting-up of the third fixation target light source 120 and the lighting-up of the fourth fixation target light source 122 to be perceived through the subject's eye 38 by the subject as a continuous lighting-up due to the afterimage effect. Accordingly, according to the ocular fundus examination device 10B, in a case in which the emitted light (the signal light here as an example) is emitted onto the second emitted-onto region β to capture an image, the fixation target can be seen by the subject without interruption.

Third Exemplary Embodiment

In the second exemplary embodiment above, four light sources were employed for achieving presentation of the fixation target to the subject in a case in which the imaging area was expanded from the first emitted-onto region α to the second emitted-onto region β. However, in order to maintain gaze fixation when imaging the peripheral region of the retina, the addition of further fixation target light sources may in some cases be impractical due to space limitations within the ocular fundus examination device. A third exemplary embodiment employing three light sources to display the fixation target to the subject, which can be useful in such cases, will now be described.

Note that in the present third exemplary embodiment, the same reference numerals are allocated to configuration elements that are the same as the configuration elements explained in the first and second exemplary embodiments above, and explanation thereof is omitted. Explanation primarily focuses on the portions that differ from the exemplary embodiments above.

Figure 13:
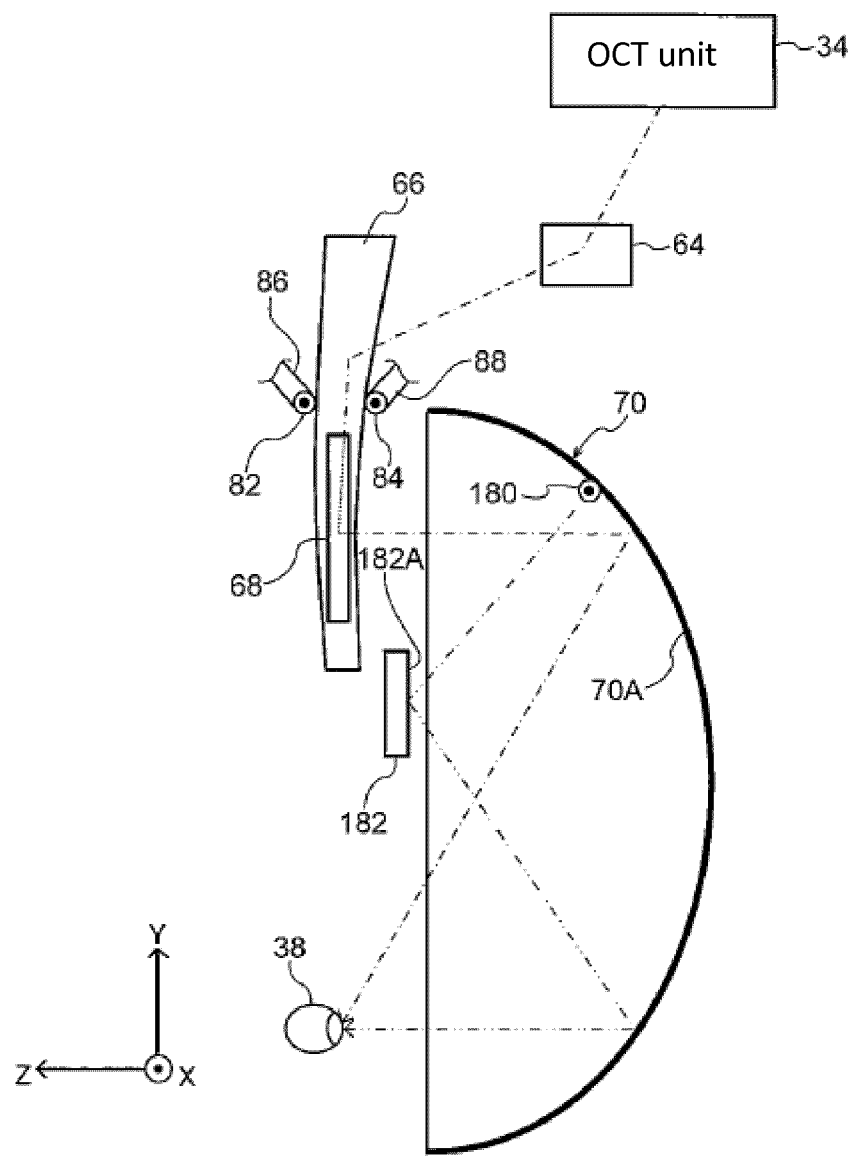
FIG. 13 is a conceptual plan view diagram illustrating a schematic configuration of a dichroic mirror, a slit mirror, an H-galvanometer mirror, an ellipsoid mirror, a planar mirror, and a first to a third fixation target light source included in an ocular fundus examination device according to the third exemplary embodiment.

The ocular fundus examination device 10C according to the present third exemplary embodiment (see FIG. 1) differs from the ocular fundus examination device 10B explained in the second exemplary embodiment above in that the ocular fundus examination device 10C does not include the fourth fixation target light source 122 or the frames 124, 126, as illustrated as an example in FIG. 13.

Moreover, the ocular fundus examination device 10C differs from the ocular fundus examination device 10B in that the ocular fundus examination device 10C includes a planar mirror 182, and in that the ocular fundus examination device 10C includes a third fixation target light source 180 instead of the third fixation target light source 120, as illustrated as an example in FIG. 13.

Figure 14:
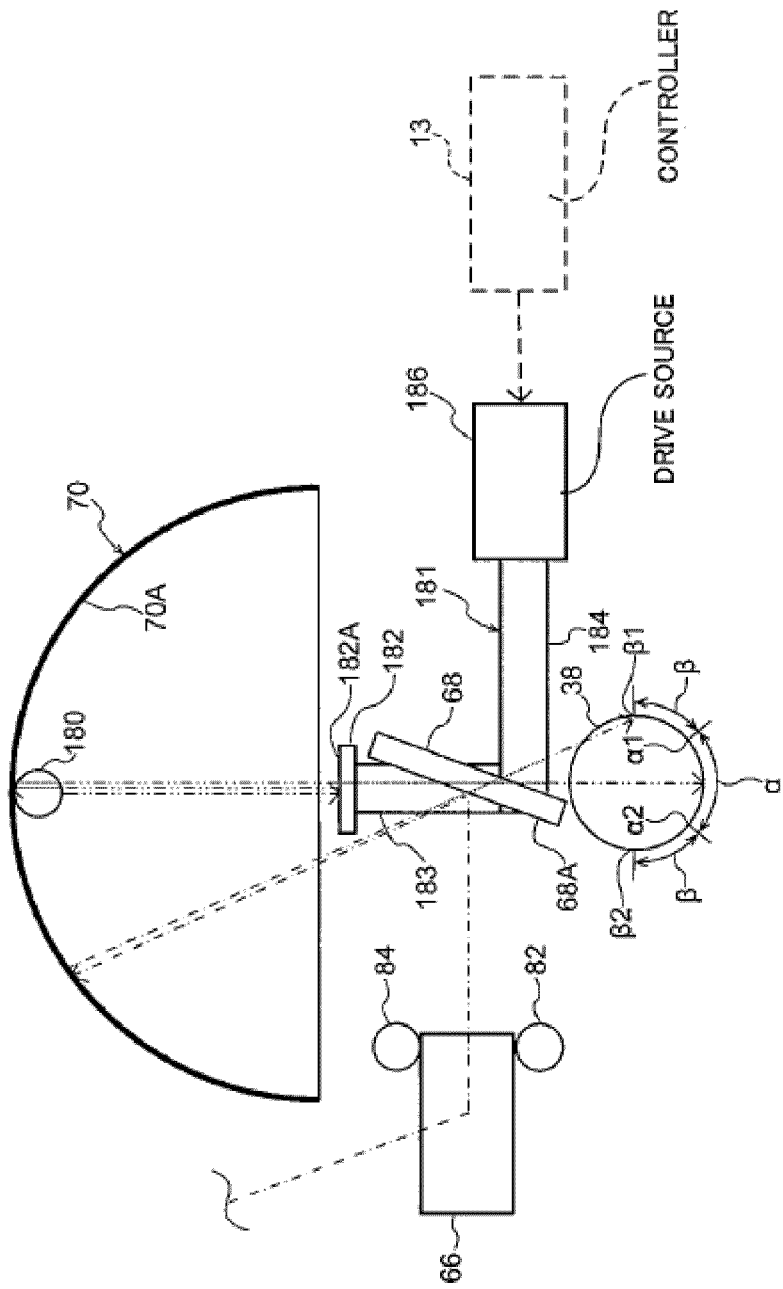
FIG. 14 is a conceptual plan view diagram illustrating an example of relevant configuration according to technology disclosed herein at a lighting-up timing in a state in which a third fixation target light source included in an ocular fundus examination device according to the third exemplary embodiment is emitting emitted light onto a third end portion.
Figure 15:
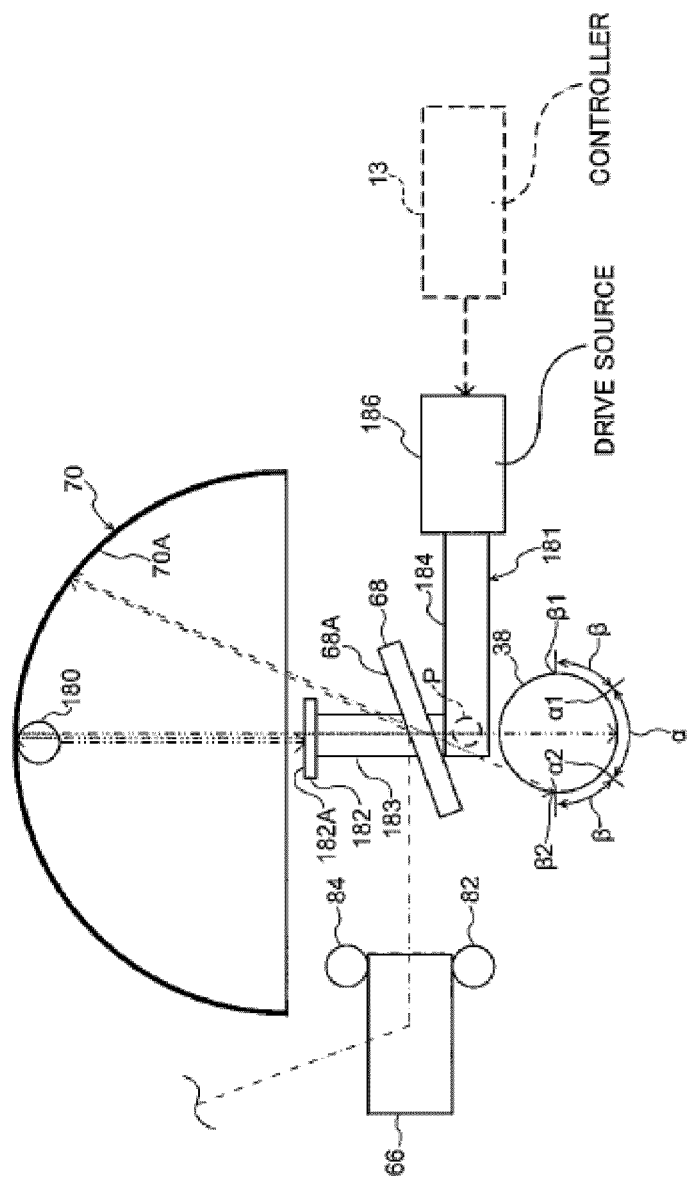
FIG. 15 is a conceptual plan view diagram illustrating an example of relevant configuration according to technology disclosed herein at a lighting-up timing in a state in which a third fixation target light source included in an ocular fundus examination device according to the third exemplary embodiment is emitting emitted light onto a fourth end portion.
Figure 16:
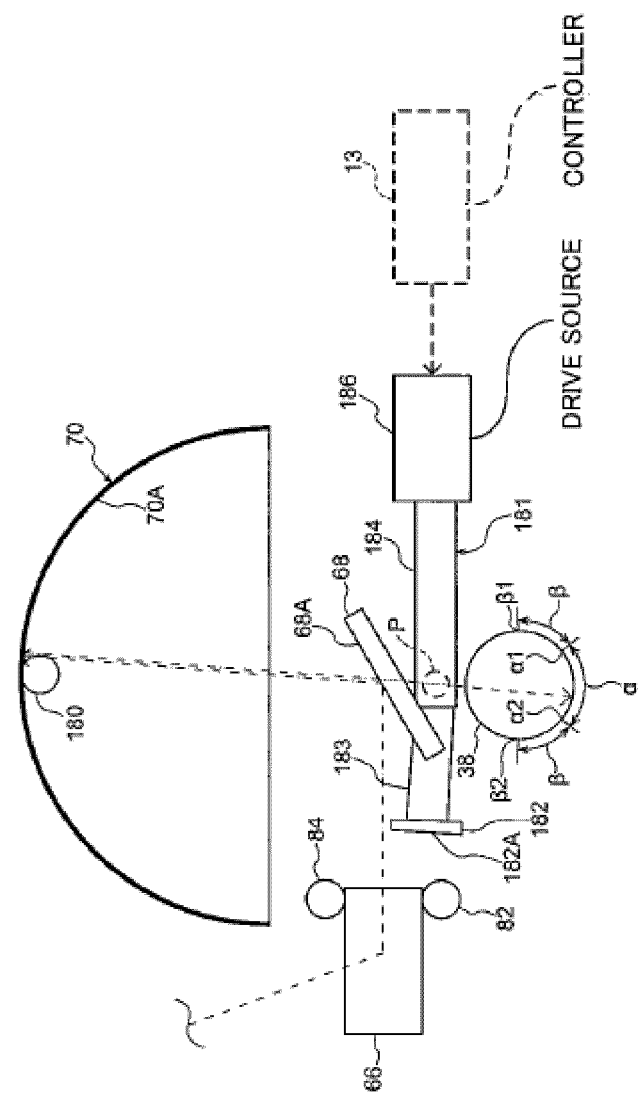
FIG. 16 is a conceptual plan view diagram illustrating an example of relevant configuration according to technology disclosed herein in a state in which a third fixation target light source included in an ocular fundus examination device according to the third exemplary embodiment is extinguished.

Moreover, the ocular fundus examination device 10C may, as in the present embodiment, differ from the ocular fundus examination device 10B in that the ocular fundus examination device 10C may include a link mechanism 181 and a drive source 186, as illustrated as an example in FIG. 14 to FIG. 16.

The ocular fundus examination device 10C also differs from the ocular fundus examination device 10B in that the secondary storage section 78 stores a program 80C instead of the program 80B, as illustrated as an example in FIG. 3.

The third fixation target light source 180 is an example of a "light source" according to technology disclosed herein. The third fixation target light source 180 is an LED that emits fixation target light having the same optical characteristics, such as amount of light, wavelength, and beam diameter, as the first fixation target light source 82 and the second fixation target light source 84. The third fixation target light source 180 is selectively lit up and lit out under control by the controller 13.

In the present third exemplary embodiment, the fixation target light is broadly split into the first fixation target light, the second fixation target light, and a third fixation target light emitted from the third fixation target light source 180. Note that for convenience of explanation in the present third exemplary embodiment, the first to the third fixation target lights are simply referred to as the "fixation target light" in a case in which explanation does not distinguish between these. Moreover, in FIG. 13 to FIG. 16, the optical path indicated by the single-dotted dashed line is the optical path of the emitted light, and the optical path of the fixation target light is indicated by the double-dotted dashed line.

As illustrated as an example in FIG. 13, the third fixation target light source 180 is disposed on the mirror face 70A of the ellipsoid mirror 70 at a position separated from the optical path of the emitted (scanning) light, and is fixed to the mirror face 70A. In particular, the optical path of the third fixation target light from the third fixation target light source 180 does not pass to the ocular fundus of the subject's eye 38 via the mirror face 68A.

As illustrated as an example in FIG. 14 to FIG. 16, the ocular fundus examination device 10C may, as in the present embodiment, include the link mechanism 181, which is an example of a "moving mechanism" according to technology disclosed herein. Moreover, the ocular fundus examination device 10C may include a drive source 186 that generates and outputs a driving force under control by the controller 13. Note that in the present third exemplary embodiment, a solenoid is applied as an example of the drive source 186; however, technology disclosed herein is not limited thereto, and, for example, this can be replaced by another drive source such as a stepping motor.

The link mechanism 181 includes a drive transmission arm 184 and a rotating member 183. As illustrated as an example in FIG. 15 and FIG. 16, a base end portion of the rotating member 183 is axially supported on a leading end portion of the drive transmission arm 184 by a rotation shaft P, and the planar mirror 182 is fixed to a leading end of the rotating member 183.

The base end portion of the drive transmission arm 184 is connected to the drive source 186, and the drive transmission arm 184 moves a mirror face 182A of the planar mirror 182 between a first position and a second position by transmitting the drive force generated by the drive source 186 to the rotating member 183. Note that the mirror face 182A is an example of a "second reflecting face" according to technology disclosed herein. Here, the planar mirror 182 that includes the mirror face 182A formed in a planar shape is given as an example; however, the present invention is not limited thereto. For example, a mirror including a mirror face formed with a convex face shape, a concave face shape, or the like may be employed instead of the planar mirror 182 to enable emission of the fixation target light in a state facing the central portion of the ocular fundus.

Note that in the present third exemplary embodiment, the first position refers to a position where the mirror face 182A reflects the third fixation target light and the reflected third fixation target light is emitted in a state facing the ocular fundus via the mirror face 70A, in a case in which the orientation of the mirror face 68A is the third orientation or the fourth orientation explained in the second exemplary embodiment above. The second position refers to a position separated from the optical path of the emitted light in a case in which the emitted light is emitted onto the first emitted-onto region α.

Since a solenoid is employed as the drive source 186 in the present third exemplary embodiment, the mirror face 182A is moved between the first position and the second position by converting a straight advancing force of the solenoid core into a rotational force using the link mechanism 181.

As illustrated as an example in FIG. 14, the third fixation target light source 180 is disposed such that the third fixation target light is emitted onto the central portion of the first emitted-onto region α in a state facing the ocular fundus when the orientation of the mirror face 68A is the third orientation.

The third fixation target light is emitted onto the central portion of the first emitted-onto region α in a state facing the ocular fundus via the mirror face 68A and the mirror face 70A in a case in which the orientation of the mirror face 68A is the third orientation. Namely, in a case in which the orientation of the mirror face 68A is the third orientation, the third fixation target light is reflected by the mirror face 182A, the reflected third fixation target light is further reflected by the mirror face 70A, and the third fixation target light reflected by the mirror face 70A arrives at the central portion of the first emitted-onto region α in a state facing the ocular fundus. Thus, the third fixation target light is not reflected by the mirror face 68A.

As illustrated as an example in FIG. 15, the third fixation target light source 180 is disposed such that the fourth fixation target light is emitted onto the central portion of the first emitted-onto region α in a state facing the ocular fundus when the orientation of the mirror face 68A is the fourth orientation explained in the second exemplary embodiment above.

In a case in which the orientation of the mirror face 68A is the fourth orientation, the fourth fixation target light is emitted onto the central portion of the first emitted-onto region α in a state facing the ocular fundus via the mirror face 182A and the mirror face 70A. Namely, in a case in which the orientation of the mirror face 68A is the fourth orientation, the fourth fixation target light is reflected by the mirror face 182A, the reflected fourth fixation target light is further reflected by the mirror face 70A, and the fourth fixation target light reflected by the mirror face 70A arrives at the central portion of the first emitted-onto region α in a state facing the ocular fundus. Thus, the fourth fixation target light is not reflected by the mirror face 68A.

The third fixation target light source 180 is lit up only in a case in which the orientation of the mirror face 68A is the third orientation or the fourth orientation.

As illustrated as an example in FIG. 16, in a case in which the orientation of the mirror face 68A is neither the third orientation nor the fourth orientation, namely, in a case in which, for example, the emitted light is not emitted onto the third end portion β1 or the fourth end portion β2, the mirror face 182A adopts a state withdrawn from the second position, and the third fixation target light source 180 is lit out.

Figure 17:
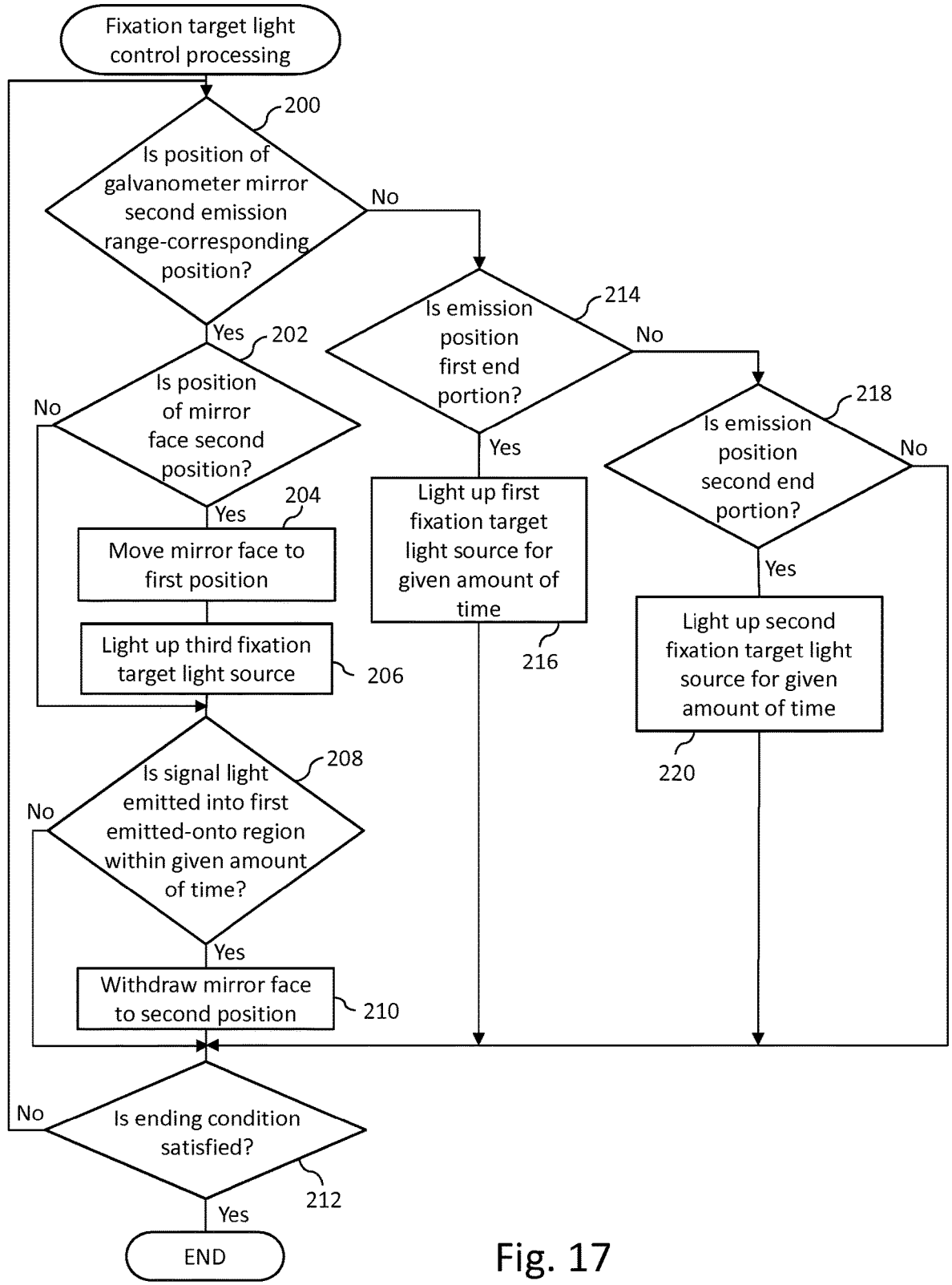
FIG. 17 is a flowchart illustrating an example of a flow of fixation target light control processing according to the third exemplary embodiment.

Next, explanation follows, with reference to FIG. 17, regarding the fixation target light control processing executed by the CPU 74 by the CPU 74 following the program 80C in a case in which the ocular fundus is imaged in the OCT mode, as operation of a portion of the ocular fundus examination device 10C according to technology disclosed herein.

In the fixation target light control processing illustrated in FIG. 17, first, at step 200, the CPU 74 determines whether or not the position of the H-galvanometer mirror 68 is a second emission range-corresponding position. Here, second emission range-corresponding position refers to a position of the H-galvanometer mirror 68 when the signal light is emitted onto the second emitted-onto region β.

At step 200, in a case in which the position of the H-galvanometer mirror 68 is the second emission range-corresponding position, affirmative determination is made and processing transitions to step 202. At step 200, in a case in which the position of the H-galvanometer mirror 68 is not the second emission range-corresponding position, negative determination is made and processing transitions to step 214.

At step 202, the CPU 74 determines whether or not the position of the mirror face 182A of the planar mirror 182 is the second position. At step 202, in a case in which the position of the mirror face 182A of the planar mirror 182 is the second position, affirmative determination is made and processing transitions to step 204. At step 202, in a case in which the position of the mirror face 182A of the planar mirror 182 is not the second position, negative determination is made and processing transitions to step 208.

At step 204, the CPU 74 moves the mirror face 182A of the planar mirror 182 to the first position by controlling the drive source 186, and then processing transitions to step 206.

At step 206, the CPU 74 illuminates the third fixation target light source 180 for a given amount of time (for example, for the same amount of lighting-up time as the first fixation target light source 82 explained in the first exemplary embodiment above) and then processing transitions to step 208.

At step 208, the CPU 74 determines whether or not the signal light is emitted into the first emitted-onto region α within the given amount of time. Note that the "given amount of time" at the present step 208 refers to an amount of time predetermined from results of tests using a real device or a computer simulation or the like, as the amount of time needed until the mirror face 182A of the planar mirror 182 withdraws from the first position to the second position.

At step 208, in a case in which the signal light is emitted into the first emitted-onto region α within the given amount of time, affirmative determination is made and processing transitions to step 210. At step 208, in a case in which the signal light is not emitted into the first emitted-onto region α within the given amount of time, negative determination is made and processing transitions to step 212.

At step 210, the CPU 74 withdraws the mirror face 182A of the planar mirror 182 to the second position by controlling the drive source 186, and processing then transitions to step 212.

At step 214, the CPU 74 determines whether or not the position on the ocular fundus the signal light is emitted onto is the first end portion α1. At step 214, in a case in which the position on the ocular fundus the signal light is emitted onto is first end portion α1, affirmative determination is made and processing transitions to step 216. At step 214, in a case in which the position on the ocular fundus the signal light is emitted onto is not the first end portion α1, negative determination is made and processing transitions to step 218.

At step 216, the CPU 74 illuminates the first fixation target light source 82 for a given amount of time (for example, the same amount of lighting-up time as the third fixation target light source 180) and processing then transitions to step 212.

At step 218, the CPU 74 determines whether or not the position on the ocular fundus the signal light is emitted onto is the second end portion α2. At step 218, in a case in which the position on the ocular fundus the signal light is emitted onto is the second end portion α2, affirmative determination is made and processing transitions to step 220. At step 218, in a case in which the position on the ocular fundus the signal light is emitted onto is not the second end portion α2, negative determination is made and processing transitions to step 212.

At step 220, the CPU 74 lights up the second fixation target light source 84 for a given amount of time (for example, for the same amount of lighting-up time as the third fixation target light source 180) and then processing transitions to step 212.

At step 212, the CPU 74 determines whether or not the ending condition has been satisfied. At step 212, in a case in which the ending condition is not satisfied, negative determination is made and processing transitions to step 200. At step 212, in a case in which the ending condition is satisfied, affirmative determination is made and the present fixation target light control processing ends.

As explained above, in the ocular fundus examination device 10C, in a case in which the orientation of the mirror face 68A is the third orientation or the fourth orientation, the mirror face 182A is disposed at the first position and the third fixation target light is reflected by the mirror face 182A and is emitted onto the central portion of the ocular fundus. Moreover, the ocular fundus examination device 10C withdraws the mirror face 182A to the second position in a case in which the orientation of the mirror face 68A is not the third orientation or the fourth orientation. Accordingly, according to the ocular fundus examination device 10C, presentation of a fixation target corresponding to the second emitted-onto region β can be achieved.

The controller 13 may be arranged to select a light source of the light sources 82, 84 and 180 depending on the which part of the ocular fundus is being imaged by the ocular fundus examination device 10C, in order to provide (preferably central) gaze fixation for all scan fields of view. More particularly, the controller 13 may initially operate in a static fixation module to control a patient alignment module (PAM), for example, to fix the gaze of the subject's eye 38 before the ocular fundus is imaged by the ocular fundus examination device 10C. The controller 13 may then switch to operating in a dynamic fixation mode while the ocular fundus is being imaged by the ocular fundus examination device 10C, and perform processes of selecting at least one of the target fixation light sources 82, 84 and 180 to provide (central) gaze fixation during the imaging of the central or peripheral region of the ocular fundus, controlling emission of the fixation target light by the selected light source(s), and controlling the positioning of the mirror face 182A by the moving mechanism, based on information indicative of at least one of: (i) orientation of the mirror face 68A; (ii) a range over which the orientation of the mirror face 68A changes during the scan; and (iii) a speed at which the orientation of the mirror face 68A changes, such that the fixation target light emitted by the selected light source follows a predetermined optical path for fixing the gaze of the subject's eye 38.

Figure 18:
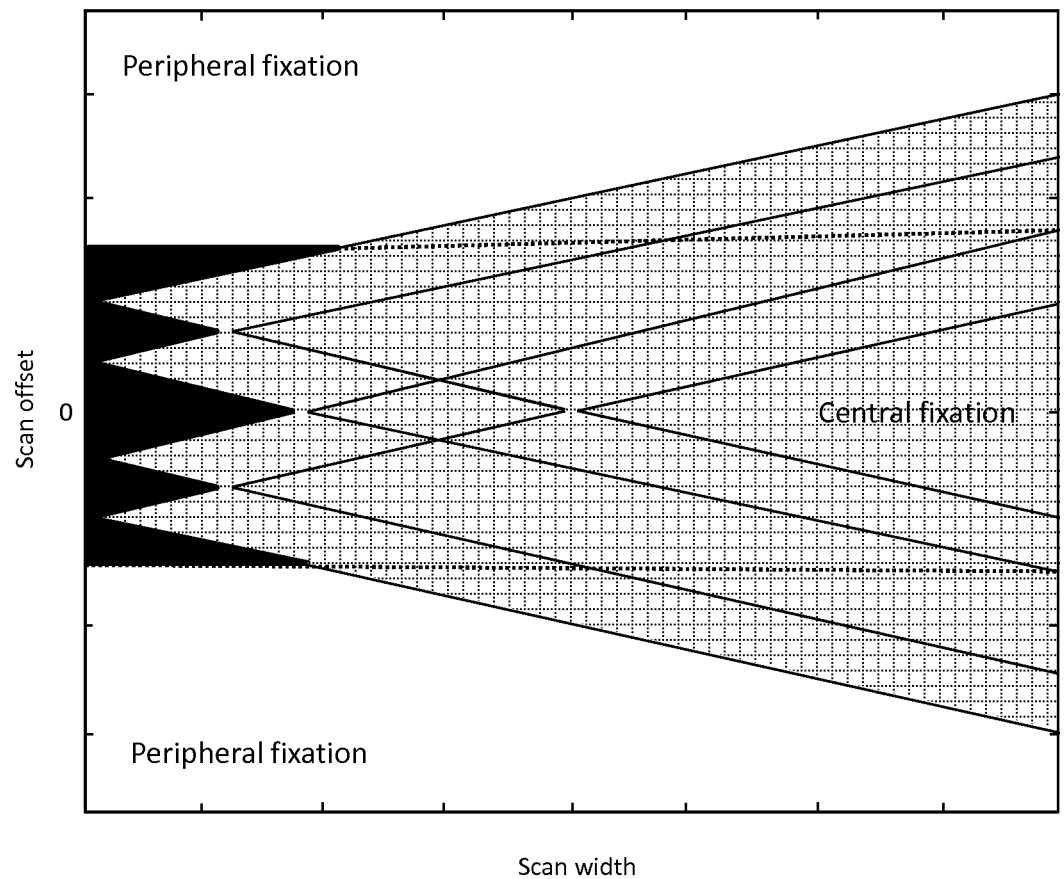
FIG. 18 shows an example fixation limit map used for the selection of a fixation target light source.

The controller 13 may use a "fixation limit map" as described herein to select a fixation target light source and set the position of the mirror face 182A. The fixation limit map defines regions in a two-dimensional space spanned by H-galvanometer mirror orientation (herein also referred to as "scan offset") as a first variable, and range of orientations of the H-galvanometer mirror 68 (herein also referred to as "scan width") achieved during the scan as a second variable, each region being associated with one or more of the fixation target light sources that are appropriate for use in the ranges of scan offset and scan width spanning the region. For example, in an embodiment which combines the four fixation target light sources 82, 84, 120 and 122 of the second embodiment with the fixation target light source 180 of the present embodiment, the controller 13 may use a stored fixation limit map as illustrated in FIG. 18 to select a fixation target light source for gaze fixation. The fixation limit map may be obtained determining the respective orientations of the H-galvanometer mirror 68 that allow the fixation lights from the fixation target light sources to follow the respective predetermined optical paths for fixing the gaze of the subject's eye, and using this information to determine which of the fixation target light source(s) may be used for each considered combination of H-galvanometer mirror orientation (scan offset) and range of orientations of the H-galvanometer mirror 68 (scan width) achieved during the scan. The exemplary fixation limit map illustrated in FIG. 18 has regions where central fixation using one or more of the fixation target light source 82, 84, 120 and 122 may be used (which are shaded in FIG. 18), regions in which peripheral fixation using the fixation target light source 180 with the planar mirror 182 in the first position may be used (unshaded in FIG. 18), and regions in which two or more of the fixation target light sources 82, 84, 120 and 122 in combination with the fixation target light source 180 and the planar mirror 182 in the first position may be used (shown between the unshaded portion and dashed line in FIG. 18). Where gaze fixation using more than one fixation target light source is possible according to the fixation limit map, one or more of those fixation target light sources may be selected in accordance with a predetermined hierarchy (in other words, assigned priorities). The turn-on period of each fixation target light source 82, 84, 120, 122 and 180 may also be determined, with the minimum "on" period being determined by the blurring effect due to the movement of the H-galvanometer mirror 68.

The controller 13 may use the stored fixation limit map to determine whether the scan parameters (scan offset and scan width) satisfy the condition for central fixation and/or peripheral fixation. If the condition for peripheral fixation is satisfied, the controller 13 may control the moving mechanism to set the mirror face 182A in the first position, and turn on the third fixation target light source 180. On the other hand, if central fixation using one of the fixation target light sources 82, 84, 120 and 122 is selected using the fixation limit map and the predetermined hierarchy, the selected fixation target light source is controlled by the controller 13 to turn on at the appropriate H-galvanometer mirror orientation, as described above. The fixation target light source being used for gaze fixation may be changed dynamically, as the scan location changes during imaging of the subject's eye 38.

Figure 21:
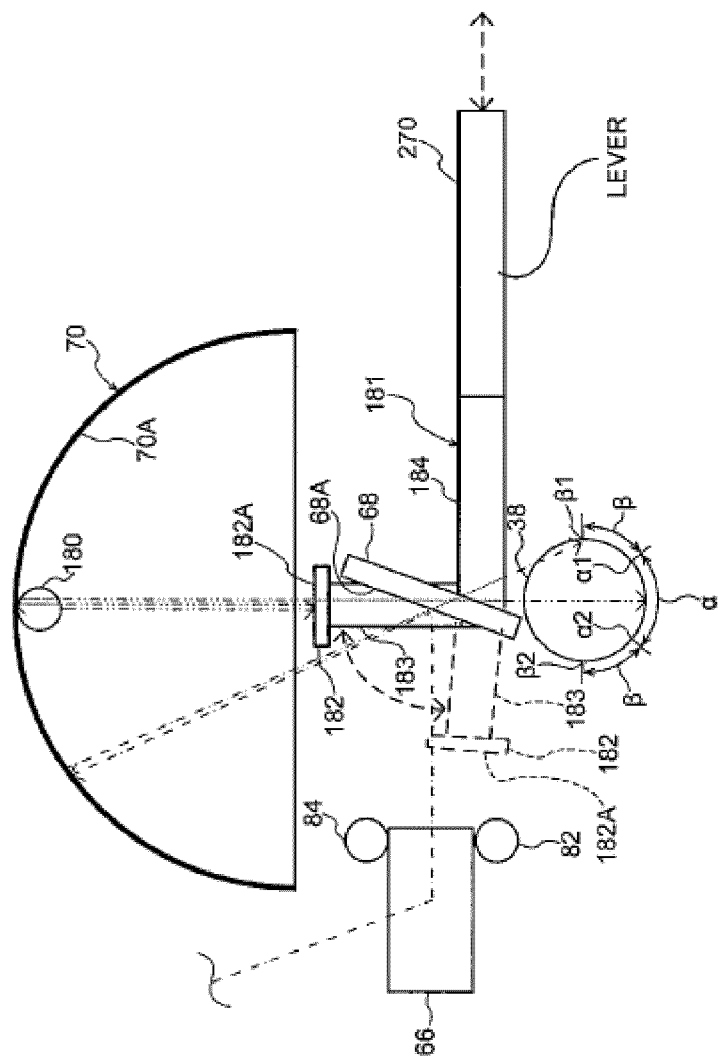
FIG. 21 is a conceptual plan view diagram illustrating a modified example of configuration of an ocular fundus examination device according to the third exemplary embodiment.

Note that in the third exemplary embodiment above, the drive force generated by the drive source 186 is transmitted to the link mechanism 181 so as to move the mirror face 182A between the first position and the second position; however, technology disclosed herein is not limited thereto. For example, as illustrated in FIG. 21, a manual lever 270 may be applied instead of the drive source 186.

In such cases, one end portion of the manual lever 270 is fixed to the base end portion of the drive transmission arm 184 of the link mechanism 181, and moving the lever 270 in the dashed line arrow direction causes the rotating member 183 to rotate, and moves the mirror face 182A between the first position and the second position. Then, the third fixation target light source 180 is lit up in a state in which the mirror face 182A is disposed at the first position. Note that the planar mirror 182 may be detected by a sensor (not illustrated in the drawings) in a case in which the mirror face 182A has moved to the first position, and the third fixation target light source 180 may be lit up under control of the controller 13 in cases in which the planar mirror 182 has been detected by the sensor. Moreover, the third fixation target light source 180 may be lit up in accordance with a specific instruction received by the reception device 22. According to the configuration illustrated as an example in FIG. 21, in a case in which the ocular fundus is imaged using the SLO mode, the third fixation target light is seen by the subject prior to imaging such that the gaze of the subject can be fixed.

Fourth Exemplary Embodiment

Explanation has been given regarding a case in which the position of the third fixation target light source 180 is fixed in the third exemplary embodiment above, however, in the present fourth exemplary embodiment, explanation follows regarding a case in which a movable third fixation target light source 232 (see FIG. 19) is employed.

Note that in the present fourth exemplary embodiment, configuration elements the same as the configuration elements explained in the first to the third exemplary embodiments above are allocated the same reference numerals and explanation thereof is omitted. Explanation primarily focuses on the portions that differ from the exemplary embodiments above.

Figure 19:
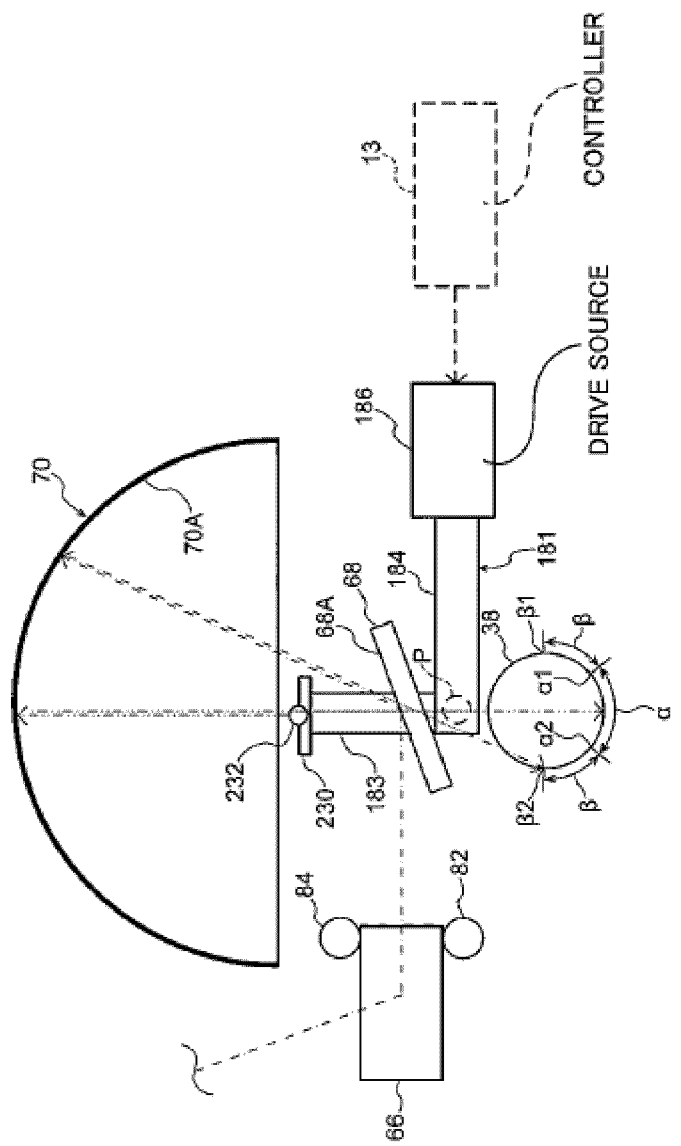
FIG. 19 is a conceptual plan view diagram illustrating an example of relevant configuration according to technology disclosed herein at a lighting-up timing in a state in which a third fixation target light source included in an ocular fundus examination device according to the fourth exemplary embodiment is emitting emitted light onto a fourth end portion.

The ocular fundus examination device 10D (see FIG. 1) according to the present fourth exemplary embodiment differs from the ocular fundus examination device 10C according to the third exemplary embodiment above in that the ocular fundus examination device 10D includes a platform 230 instead of the planar mirror 182, as illustrated as an example in FIG. 19.

The ocular fundus examination device 10D also differs from the ocular fundus examination device 10C in that the ocular fundus examination device 10D includes a third fixation target light source 232 instead of the third fixation target light source 180.

The ocular fundus examination device 10D also differs from the ocular fundus examination device 10C in that the secondary storage section 78 stores a program 80D instead of the program 80C, as illustrated as an example in FIG. 3.

As illustrated as an example in FIG. 19, the ocular fundus examination device 10D may, as in the present embodiment, be provided with a platform 230 that is fixed to a leading end of the rotating member 183, and the third fixation target light source 232 may be fixed to a central portion of the platform 230.

The characteristics of the fixation target light of the third fixation target light source 232 are the same as the characteristics of the fixation target light of the third fixation target light source 180 explained in the third exemplary embodiment above, and the third fixation target light source 232 is selectively lit up and lit out under control by the controller 13.

In the present fourth exemplary embodiment, the fixation target light is broadly split into the first fixation target light, the second fixation target light, and a third fixation target light emitted from the third fixation target light source 232. Note that for convenience of explanation in the fourth exemplary embodiment, the first to the third fixation target lights are simply referred to as the "fixation target light" in a case in which explanation does not distinguish between these. Moreover, in FIG. 19, the optical path indicated by the single-dotted dashed line is the optical path of the emitted light, and the optical path of the fixation target light is indicated by the double-dotted dashed line.

a drive transmission arm 184 may move the third fixation target light source 232 between a first position (for example, the position illustrated in FIG. 19) and a second position by transmitting the drive force generated by the drive source 186 to the rotating member 183. Here, the first position refers to a position at which the third fixation target light emitted from the third fixation target light source 232 is reflected by the mirror face 70A and the reflected third fixation target light is emitted in a state facing the ocular fundus, in a case in which the orientation of the mirror face 68A is the third orientation or the fourth orientation explained in the second exemplary embodiment above. The second position refers to a position separated from the optical path of the emitted light in a case in which the emitted light is emitted onto the first emitted-onto region α.

In a case in which the orientation of the mirror face 68A is the third orientation, the third fixation target light source 232 is disposed at the first position, the third fixation target light from the third fixation target light source 232 is reflected by the mirror face 70A, and the third fixation target light reflected by the mirror face 70A arrives at the central portion of the first emitted-onto region α in a state facing the ocular fundus.

In a case in which the orientation of the mirror face 68A is the fourth orientation, the third fixation target light source 232 is disposed at the first position, the third fixation target light from the third fixation target light source 232 is reflected by the mirror face 70A, and the third fixation target light reflected by the mirror face 70A arrives at the central portion of the first emitted-onto region α in a state facing the ocular fundus.

The third fixation target light source 232 is lit up only in a case in which the orientation of the mirror face 68A is the third orientation or the fourth orientation.

Note that in a case in which the orientation of the mirror face 68A is the third orientation or the fourth orientation, namely, in a case in which, for example, the emitted light is not emitted onto the third end portion β1 or the fourth end portion β2, the third fixation target light source 232 adopts a state withdrawn from the second position, and the third fixation target light source 232 is lit out.

Figure 20:
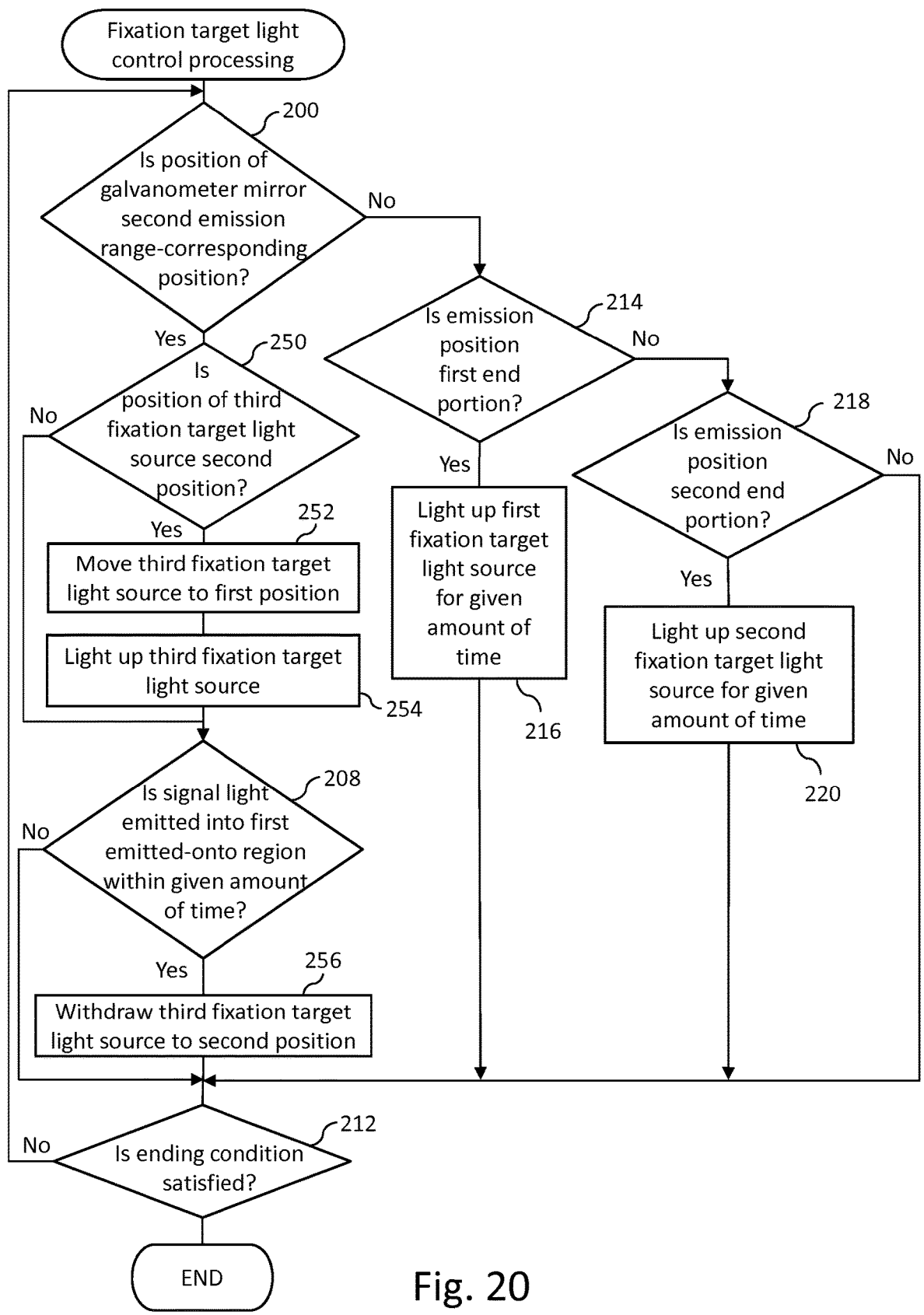
FIG. 20 is a flowchart illustrating an example of a flow of fixation target light control processing according to the fourth exemplary embodiment.

Next, explanation follows, with reference to FIG. 20, regarding the fixation target light control processing executed by the CPU 74 by the CPU 74 following the program 80D in a case in which the ocular fundus is imaged in the OCT mode, as operation of a portion of the ocular fundus examination device 10D according to technology disclosed herein. Note that steps the same as steps of the flowchart illustrated in FIG. 17 are allocated the same reference numerals, and explanation thereof is omitted.

The fixation target light control processing illustrated in FIG. 20 differs from the fixation target light control processing illustrated in FIG. 17 in that steps 250 to 254 are included instead of steps 202 to 206, and in that step 256 is included instead of step 210.

At step 250, the CPU 74 determines whether or not the position of the third fixation target light source 232 is the second position. At step 250, in a case in which the position of the third fixation target light source 232 is the second position, affirmative determination is made and processing transitions to step 252. At step 250, in a case in which the position of the third fixation target light source 232 is not the second position, negative determination is made and processing transitions to step 208.

At step 252 the CPU 74 moves the third fixation target light source 232 to the first position by controlling the drive source 186, and processing then transitions to step 254.

At step 254, the CPU 74 lights up the third fixation target light source 232 for a given amount of time (for example, the same amount of lighting-up time as the first fixation target light source 82 explained in the first exemplary embodiment above), and processing then transitions to step 208.

At step 256, the CPU 74 withdraws the third fixation target light source 232 to the second position by controlling the drive source 186, and processing then transitions to step 212.

As explained above, in the ocular fundus examination device 10D, in a case in which the orientation of the mirror face 68A is the third orientation or the fourth orientation, the third fixation target light source 232 is disposed at the first position and the third fixation target light is reflected by the mirror face 70A and is emitted onto the central portion of the ocular fundus. Moreover, the ocular fundus examination device 10D withdraws the third fixation target light source 232 to the second position in a case in which the orientation of the mirror face 68A is not the third orientation or the fourth orientation. Accordingly, according to the ocular fundus examination device 10D, presentation of a fixation target corresponding to the second emitted-onto region β, which is the peripheral portion of the ocular fundus, can be achieved.

Similar to the third embodiment described above, the controller 13 may be arranged to use the fixation limit map of the kind illustrated in FIG. 18 to select a light source of the light sources 82, 84 and 232, control emission of the fixation target light by the selected light source, and control the positioning of the third fixation target light source 232 by the moving mechanism, based on information indicative of at least one of: (i) the orientation of the mirror face 68A; (ii) a range of orientation of the mirror face 68A; and (iii) a speed at which the orientation of the mirror face 68A changes, such that the fixation target light emitted by the selected light source follows a predetermined optical path for fixing the gaze of the subject's eye 38.

Figure 22:
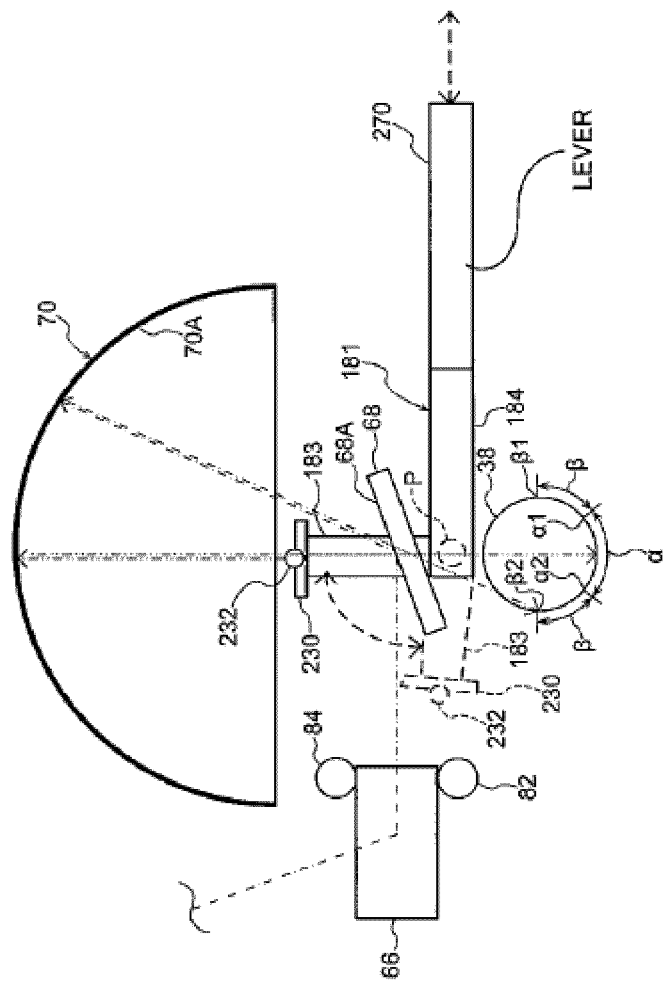
FIG. 22 is a conceptual plan view diagram illustrating a modified example of configuration of an ocular fundus examination device according to the fourth exemplary embodiment.

Note that in the fourth exemplary embodiment above, the drive force generated by the drive source 186 is transmitted to the link mechanism 181 so as to move the third fixation target light source 232 between the first position and the second position; however, technology disclosed herein is not limited thereto. For example, as illustrated in FIG. 22, a manual lever 270 may be applied instead of the drive source 186.

In such cases, one end portion of the manual lever 270 is fixed to the base end portion of the drive transmission arm 184 of the link mechanism 181, and moving the lever 270 in the dashed line arrow direction causes the rotating member 183 to rotate, and moves the third fixation target light source 232 between the first position and the second position. Then, the third fixation target light source 232 is lit up in a state in which the third fixation target light source 232 is disposed at the first position. Note that the third fixation target light source 232 or the platform 230 may be detected by a sensor (not illustrated in the drawings) in a case in which the third fixation target light source 232 has moved to the first position, and the third fixation target light source 232 may be illuminated under control of the controller 13 in a case in which the third fixation target light source 232 or the platform 230 has been detected by the sensor. Moreover, the third fixation target light source 232 may be lit up in accordance with a specific instruction received by the reception device 22. According to the configuration illustrated as an example in FIG. 22, in a case in which the ocular fundus is imaged using the SLO mode, the third fixation target light is seen by the subject prior to imaging such that the gaze of the subject can be fixed.

Although examples have been given in each of the exemplary embodiments above in which a pair of concave mirrors are configured by the slit mirror 66 and the ellipsoid mirror 70, the present invention is not limited thereto. For example, an angled spherical mirror, a non-spherical mirror, a pair of parabola mirrors, a pair of parabolic mirrors, a lens system, or an optical system employing an appropriate combination of these may be employed instead of the slit mirror 66.

Figure 23:
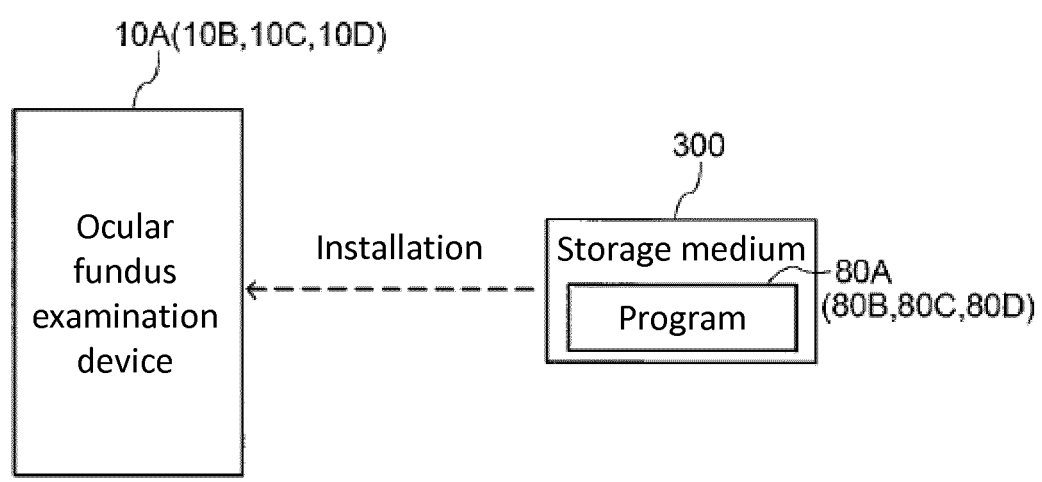
FIG. 23 is a conceptual diagram illustrating an example of an aspect in which a program is installed to an ocular fundus examination device from a storage medium storing a program according to a first to a fourth exemplary embodiment.

Although examples have been given of cases in which the program 80A, 80B, 80C, 80D (referred to simply as the "program 80A etc." hereafter) of each of the exemplary embodiments above are read from the secondary storage section 78, the program 80A etc. does not necessarily need to be stored on the secondary storage section 78 from the outset. For example, as illustrated in FIG. 23, the program 80A etc. may first be stored to a freely selected portable storage medium 300, such as a solid state drive (SSD), universal serial bus (USB) memory, or a compact disc read only memory (CD-ROM). In such cases, the program 80A etc. of the storage medium 300 is installed to the ocular fundus examination device 10A (10B, 10C, 10D) (referred to as the "ocular fundus examination device 10A etc." hereafter), and the installed program is executed by the CPU 74.

The program 80A etc. may be stored in a storage section of another computer, server device, or the like connected to the ocular fundus examination device 10A etc. through a communication network (not illustrated in the drawings), and the program 80A etc. may be downloaded in accordance with a request by the ocular fundus examination device 10A etc. In such cases, the downloaded program 80A etc. is executed by the CPU 74.

Moreover, the fixation target light control processing explained in each of the exemplary embodiments above are merely examples. It therefore goes without saying that unnecessary steps may be omitted, new steps may be added, and the processing sequence may be rearranged within a range not departing from the spirit of the present disclosure. Moreover, each item of processing included in the fixation target light control processing may be implemented by hardware configuration alone, such as an FPGA, an ASIC, or the like, or may be implemented by a combination of a computer employing software configuration and hardware configuration.

Moreover, although explanation has been given in each of the exemplary embodiments above regarding examples in which the polygon mirror 44 that scans in the Y direction and the V-galvanometer mirror 60 that scans in the Y direction are disposed at the light incidence side of the dichroic mirror 64, the dichroic mirror 64 may be disposed at a position separated from the focal point of a slit mirror in the optical axis direction, and the polygon mirror 44 or the V-galvanometer mirror 60 that scans in the Y direction may be disposed at the focal point position of the slit mirror. In such cases, the polygon mirror 44 or the V-galvanometer mirror 60 functions as a shared scanning optical system employed during SLO image acquisition and during OCT image acquisition.

Moreover, although explanation has been given regarding an example in which a shared optical axis through which light for SLO and light for OCT passes is generated by the dichroic mirror 64, a beam splitter such as a polarizing beam splitter or an optical member such as a half mirror may be employed instead of the dichroic mirror 64.

Figure 24:
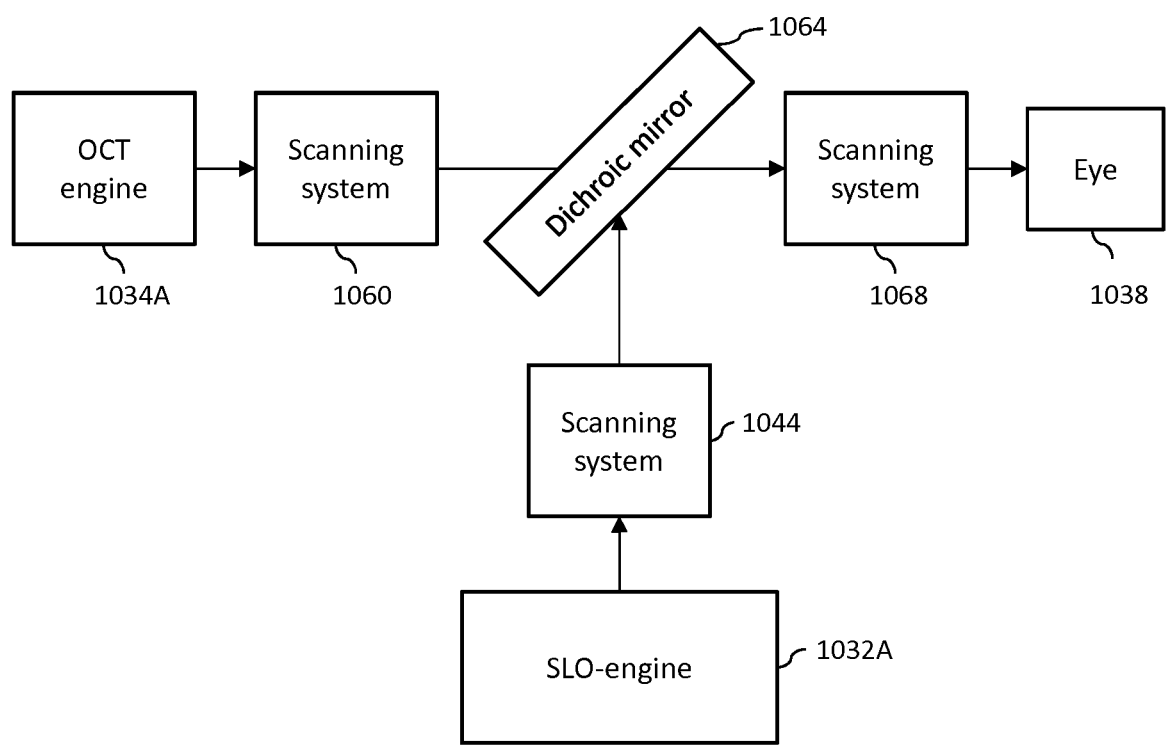
FIG. 24 is a conceptual diagram illustrating configuration corresponding to the SLO unit, the OCT unit, and the shared optical system illustrated in FIG. 1.

Explanation has been given in each of the exemplary embodiments above regarding examples in which, as illustrated in FIG. 1, the polygon mirror 44 and the V-galvanometer mirror 60 are disposed at the light incidence side of the dichroic mirror 64, and the H-galvanometer mirror 68 for X direction scanning, shared by SLO and OCT, is disposed at the light emission side of the dichroic mirror 64. FIG. 24 illustrates a configuration corresponding to the SLO unit 32, the OCT unit 34, and the shared optical system 36 illustrated in FIG. 1. As illustrated as an example in FIG. 24, a device main body includes a dichroic mirror 1064, an SLO engine 1032A, and an OCT engine 1034A. A scanning system 1044 is disposed between the dichroic mirror 1064 and the SLO engine 1032A. Moreover, a scanning system 1060 is disposed between the dichroic mirror 1064 and the OCT engine 1034A. A scanning system 1068 is disposed between the dichroic mirror 1064 and a subject's eye 1038.

Note that the scanning system 1044 corresponds to the polygon mirror 44, and the SLO engine 1032A is a portion obtained by removing the polygon mirror 44 from the SLO unit 32 in FIG. 1. The scanning system 1060 corresponds to the V-galvanometer mirror 60, and the OCT engine 1034A is a portion obtained by removing the V-galvanometer mirror 60 from the OCT unit 34 in FIG. 1. The scanning system 1068 corresponds to the H-galvanometer mirror 68.

The following modifications can be can be made to the scanning optical system.

Figure 25:
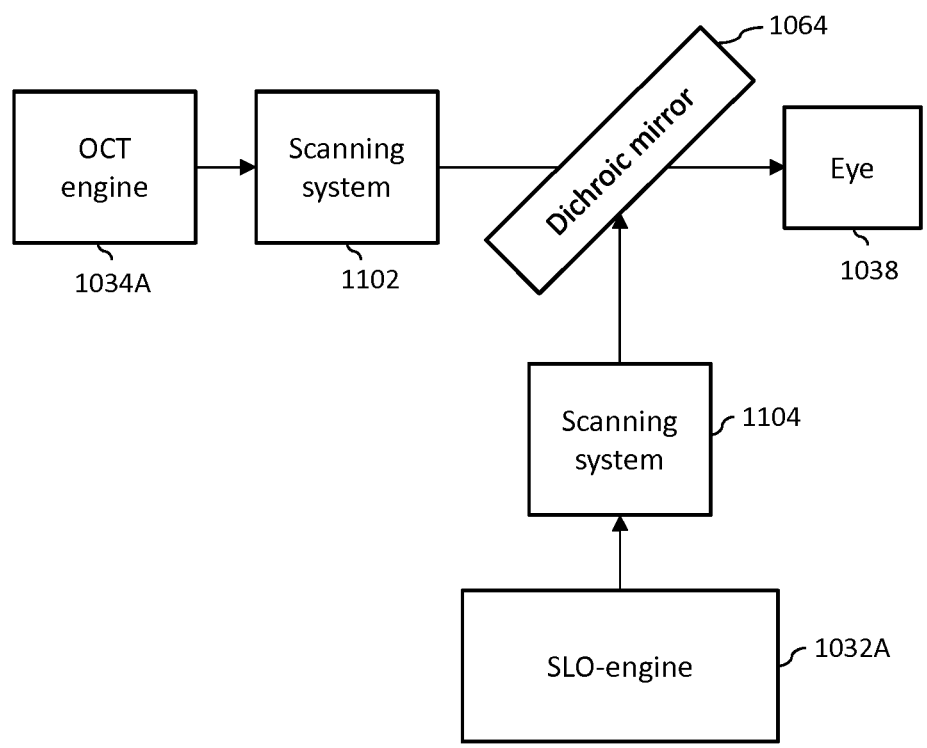
FIG. 25 is a conceptual diagram illustrating a first modified example of a scanning optical system.

FIG. 25 illustrates a first modified example of a scanning optical system. As illustrated as an example in FIG. 25, a two-dimensional scanning optical system 1104 for SLO is disposed on one light incidence side (the SLO engine 1032A side) of the dichroic mirror 1064, and a two-dimensional scanning optical system 1102 for OCT is disposed at another light incidence side (the OCT engine 1034A side) of the dichroic mirror 1064.

Figure 26:
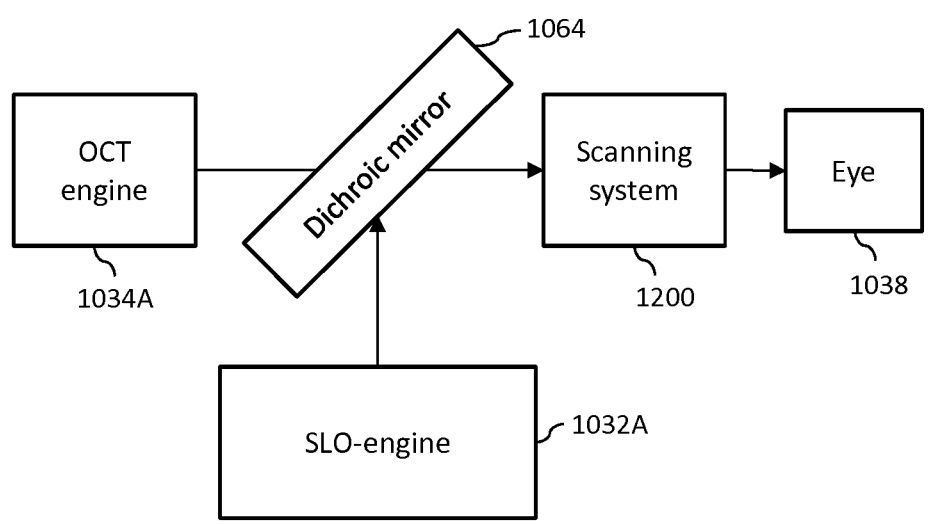
FIG. 26 is a conceptual diagram illustrating a second modified example of a scanning optical system.

FIG. 26 illustrates a second modified example of a scanning optical system. As illustrated as an example in FIG. 26, a shared two-dimensional scanning optical system 1200, employed by SLO and OCT, is disposed at the light emission side of the dichroic mirror 64.

Moreover, it also goes without saying that in the all of the scanning optical system explained above, similar scanning can be performed by exchanging the X direction with the Y direction.

Although explanation has been given regarding examples in which an ellipsoid mirror is employed as an optical member that relays the scanning, another concave mirror such as a parabolic mirror may be employed, or an optical member such as a lens may be employed instead of a concave mirror. An optical member that includes plural focal points may be employed as the optical member that relays the scanning. In such cases, the positional relationship between the optical member, the scanning optical system, and the subject's eye may adopt the following aspects.

In a first aspect, the subject's eye is disposed at one focal point position f1, and a shared two-dimensional scanning optical system, employed by SLO and OCT, is disposed at another one focal point position f2.

In a second aspect, the subject's eye is disposed at one focal point position f1, a two-dimensional scanning optical system employed by SLO is disposed at another one focal point position f2, and a two-dimensional scanning optical system employed by OCT is disposed at yet another one focal point position f3.

In a third aspect, the subject's eye is disposed at one focal point position f1, a shared one-dimensional scanning optical system employed by both SLO and OCT and scanning light in a first direction is disposed at another one focal point position f2, a one-dimensional scanning optical system that scans light in a second direction intersecting the first direction (for example, an orthogonal direction) employed by SLO is disposed at yet another one focal point position f3, and a one-dimensional scanning optical system that scans light in a second direction employed in OCT is disposed at an optically equivalent position to the another one focal point position f3.

Note that in each of the aspects above, the subject's eye and a scanning optical system may be disposed at a position optically equivalent to a focal point position instead of a focal point position.

Figure 27:
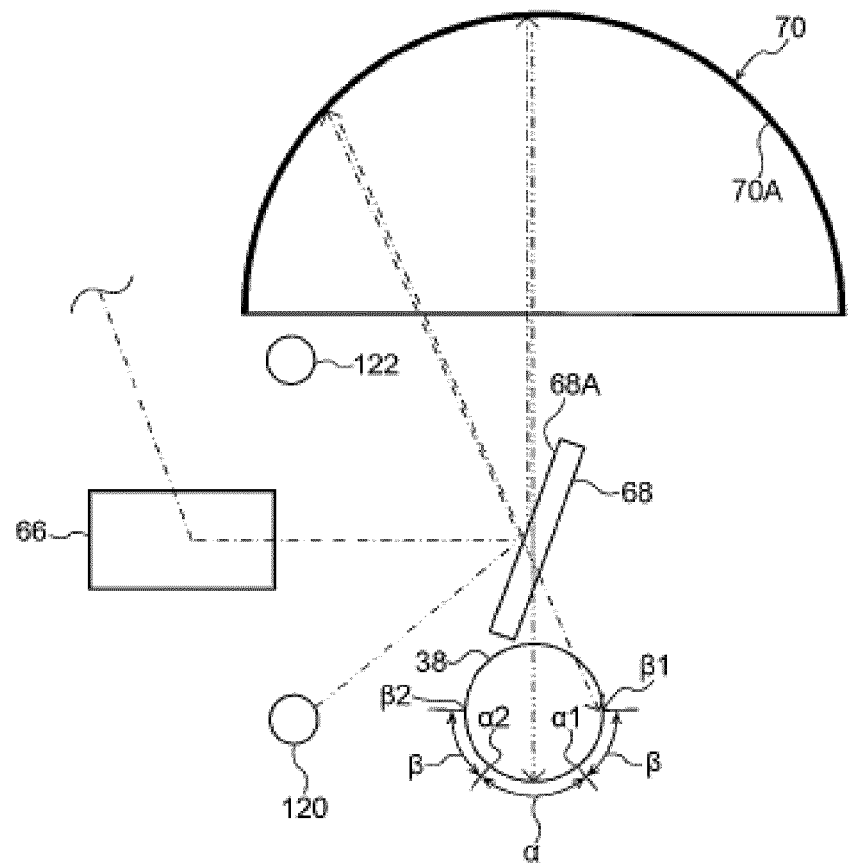
FIG. 27 is a conceptual plan view diagram illustrating a modified example of relevant configuration of an ocular fundus examination device according to the second exemplary embodiment.

An example has been given in the second exemplary embodiment above regarding a case in which the first fixation target light source 82, the second fixation target light source 84, the third fixation target light source 120, and the fourth fixation target light source 122 are selectively employed; however, technology disclosed herein is not limited thereto. For example, as illustrated in FIG. 27, the first fixation target light source 82 and the second fixation target light source 84 may be omitted, and the third fixation target light source 120 and the fourth fixation target light source 122 provided. Note that in such cases, a region defined by the first emitted-onto region α and the second emitted-onto region β, namely a region spanning from the third end portion β1 to the fourth end portion β2, corresponds to a "central region" according to technology disclosed herein, the third fixation target light source 120 operates as a "first light source" according to technology disclosed herein, and the fourth fixation target light source 122 operates as a "second light source" according to technology disclosed herein.

Moreover, the link mechanism 181 has been given as an example in the third exemplary embodiment above; however, technology disclosed herein is not limited thereto, and, for example, a shift mechanism capable of moving the mirror face 182A between the first position enabling emission of the third and fourth fixation target light in a state facing the ocular fundus and the second position separated from the optical path of the emitted light may be employed instead of the link mechanism 181. Examples of the shift mechanism include a mechanism with linear movement by receiving drive force of a solenoid or a stepping motor. The shift mechanism may move the mirror face 182A in the Z direction, may move the mirror face 182A in the X direction, or may move the mirror face 182A in the Y direction.

Likewise, the fourth exemplary embodiment may employ a shift mechanism capable of moving the third fixation target light source 232 between the first position capable of emitting the third and fourth fixation target light in a state facing the ocular fundus and the second position separated from the optical path of the emitted light.

In the first embodiment described above, the first orientation of the mirror face 68A of the H-galvanometer mirror 68 (as an example of a reflecting face) causes the light to be emitted onto the first end portion α1, which is one end portion in the specific direction of the central region of the ocular fundus. However, the first light source 82 need not be configured to emit the first fixation target light when the mirror face 68A is orientated in this particular way, and may alternatively be configured to light up when the reflecting face is orientated in a predefined orientation that may be adjusted so as to vary a location on the ocular fundus onto which fixation target light is emitted. The gaze direction of the subject's eye 38 may thus be changed to, and maintained in, a number of different directions, so that different regions of the ocular fundus of the subject's eye associated with the different gaze directions can be imaged.

All publications, patent applications and technical standards mentioned in the present specification are incorporated by reference in the present specification to the same extent as if each individual publication, patent application, or technical standard was specifically and individually indicated to be incorporated by reference.

EXPLANATION OF THE REFERENCE NUMERALS

10A, 10B, 10C, 10D ocular fundus examination device
32 SLO unit
34 OCT unit
68A, 70A, 182A mirror face
74 CPU
82 first fixation target light source
84 second fixation target light source
120, 180, 232 third fixation target light source
122 fourth fixation target light source
184 link mechanism
186 drive source
α a first emitted-onto region
α1 first end portion
α2 second end portion
β second emitted-onto region
β1 third end portion
β2 fourth end portion

The invention claimed is:

1. An ophthalmic device comprising:
a light source arranged to emit a fixation target light;
a reflecting face arranged to reflect the fixation target light, and further arranged to reflect scanning light emitted by an emission section and to scan the scanning light in a specific direction by changing orientation, wherein the emission section is a source of the scanning light that is different from the light source, and the fixation target light and the scanning light are incident on the reflecting face via different optical paths;
a concave mirror face disposed such that the scanning light reflected by the reflecting face is incident on an ocular fundus of a subject's eye when the subject's eye is placed at a focal point of the concave mirror during use of the ophthalmic device,
the ophthalmic device being arranged such that, when the subject's eye is placed at the focal point of the concave mirror during use of the ophthalmic device and when the light source emits the fixation target light, the fixation target light and the scanning light are simultaneously incident on the ocular fundus via different optical paths both propagating via the concave mirror face and the focal point, the target fixation light following a predetermined optical path for fixing a gaze of the subject's eye.

2. The ophthalmic device according to claim 1, arranged such that, when the subject's eye is placed at a focal point of the concave mirror during use of the ophthalmic device and when the light source emits the fixation target light, the fixation target light and the scanning light are simultaneously incident on the ocular fundus via different optical paths both passing via the reflecting face, the concave mirror face and the focal point, the ophthalmic device further comprising a controller arranged to control emission of the target fixation light by the light source such that the fixation target light follows the predetermined optical path for fixing the gaze of the subject's eye.

3. The ophthalmic device according to claim 2, further comprising:
at least one further light source arranged such that, when the subject's eye is placed at the focal point of the concave mirror during use of the ophthalmic device and when each of the at least one further light source emits the fixation target light, the respective fixation target light and the scanning light are simultaneously incident on the ocular fundus via different optical paths both going via the concave mirror face and the focal point, the optical path of the respective fixation target light not passing via the reflecting face,
wherein the controller is arranged to select a light source from the light sources and control emission of the fixation target light by the selected light source, based on information indicative of at least one of an orientation of the reflecting face, a range of orientation of the reflecting face, and a speed at which the orientation of the reflecting face changes, such that the fixation target light emitted by the selected light source follows a predetermined optical path for fixing the gaze of the subject's eye.

4. The ophthalmic device according to claim 2, further comprising:
at least one further light source arranged such that, when the subject's eye is placed at the focal point of the concave mirror during use of the ophthalmic device and when each of the at least one further light source emits the fixation target light, the respective fixation target light and the scanning light are simultaneously incident on the ocular fundus via different optical paths both going via the reflecting face, the concave mirror face and the focal point,
wherein the controller is arranged to select a light source from the light sources and control emission of the fixation target light by the selected light source, based on information indicative of one of an orientation of the reflecting face, a range of orientation of the reflecting face, and a speed at which the orientation of the reflecting face changes, such that the fixation target light emitted by the selected light source follows a predetermined optical path for fixing the gaze of the subject's eye.

5. The ophthalmic device according to claim 1, arranged such that, when the subject's eye is placed at the focal point of the concave mirror during use of the ophthalmic device and when each light source emits fixation target light, the respective fixation target light and the scanning light are simultaneously incident on different locations on the ocular fundus via different optical paths both going via the concave mirror face and the focal point.

6. The ophthalmic device according to claim 2, wherein the controller is arranged to control emission of the target fixation light by each light source such that the light source emits the fixation target light only when the reflecting face is orientated in a predetermined orientation, said predetermined orientation being adjustable so as to vary a location on the ocular fundus onto which the fixation target light is emitted.

7. The ophthalmic device according to claim 1, wherein the reflecting face is a first reflecting face, and wherein the ophthalmic device further comprises a second reflecting face that is disposed at a first position separated from an optical pathway of the scanning light in a case in which the scanning light is emitted onto a peripheral region of the ocular fundus, and arranged to reflect fixation target light onto the ocular fundus along the predetermined optical path via the concave mirror face when the subject's eye is placed at the focal point of the concave mirror during use of the ophthalmic device.

8. The ophthalmic device according to claim 2,
wherein the reflecting face is a first reflecting face,
wherein the ophthalmic device further comprises a second reflecting face that is disposed at a first position separated from an optical pathway of the scanning light in a case in which the scanning light is emitted onto a peripheral region of the ocular fundus, and arranged to reflect fixation target light onto the ocular fundus along the predetermined optical path via the concave mirror face when the subject's eye is placed at the focal point of the concave mirror during use of the ophthalmic device, and
wherein the second reflecting face is movable between the first position and a second position, the second position being separated from an optical pathway of the scanning light in a case in which the scanning light is emitted onto a central region of the ocular fundus, the ophthalmic device further comprising:
a moving mechanism arranged to move the second reflecting face between the first position and the second position, and
wherein the controller also is arranged to control the moving mechanism, and to control the light source that is arranged to emit the fixation target light which is reflected from the second reflecting face, such that the second reflecting face is disposed at the first position and said light source is lit up in a case in which the orientation of the first reflecting face is an orientation causing the scanning light to be emitted onto the peripheral region, and such that the second reflecting face is disposed at the second position in a case in which the orientation of the first reflecting face is an orientation causing the scanning light to be emitted onto the central region.

9. The ophthalmic device according to claim 8, wherein the controller is arranged to select a light source of the light sources, control emission of the fixation target light by the selected light source, and control the positioning of the second reflecting surface by the moving mechanism, based on information indicative of at least one of the orientation, a range of orientation of the first reflecting face, and a speed at which the orientation of the first reflecting face changes, such that the fixation target light emitted by the selected light source follows a predetermined optical path for fixing the gaze of the subject's eye.

10. The ophthalmic device according to claim 1, further comprising a second light source that is disposed at a first position separated from an optical pathway of the scanning light in a case in which the scanning light is emitted onto a peripheral region of the ocular fundus, and arranged to emit fixation target light onto the ocular fundus along a predetermined optical path via the concave mirror face when the subject's eye is placed at the focal point of the concave mirror during use of the ophthalmic device.

11. The ophthalmic device according to claim 2,
further comprising a second light source that is disposed at a first position separated from an optical pathway of the scanning light in a case in which the scanning light is emitted onto a peripheral region of the ocular fundus, and arranged to emit fixation target light onto the ocular fundus along a predetermined optical path via the concave mirror face when the subject's eye is placed at the focal point of the concave mirror during use of the ophthalmic device,
wherein the reflecting face is a first reflecting face, and the second light source is movable between the first position and a second position, the second position being separated from an optical pathway of the scanning light in a case in which the scanning light is emitted onto a central region of the ocular fundus, the ophthalmic device further comprising:
a moving mechanism arranged to move the second light source between the first position and the second position, and
wherein the controller also is arranged to control the moving mechanism and the emission of target fixation light by the second light source such that the second light source is disposed at the first position and lit up in a case in which the orientation of the first reflecting face is an orientation causing the scanning light to be emitted onto the peripheral region, and such that the second light source is disposed at the second position in a case in which the orientation of the first reflecting face is an orientation causing the scanning light to be emitted onto the central region.

12. The ophthalmic device according to claim 11, wherein the controller is arranged to select a light source of the light sources, control emission of the fixation target light by the selected light source, and control positioning of the second light source by the moving mechanism, based on information indicative of at least one of the orientation, a range of orientation of the first reflecting face, and a speed at which the orientation of the first reflecting face changes, such that the fixation target light emitted by the selected light source follows a predetermined optical path for fixing the gaze of the subject's eye.

13. The ophthalmic device according to claim 1, arranged such that, when the subject's eye is placed at the focal point of the concave mirror during use of the ophthalmic device, the light source is arranged to emit the fixation target light such that the fixation target light incident on the ocular fundus is perceived by the subject as a continuous lighting.

* * * * *